US006897025B2

(12) United States Patent
Cox et al.

(10) Patent No.: US 6,897,025 B2
(45) Date of Patent: May 24, 2005

(54) GENETIC ANALYSIS SYSTEMS AND METHODS

(75) Inventors: David R. Cox, Belmont, CA (US); Bradley A. Margus, Boca Raton, FL (US); Nila Patil, Woodside, CA (US)

(73) Assignee: Perlegen Sciences, Inc., Mountain View, CA (US)

(*) Notice: Subject to any disclaimer, the term of this patent is extended or adjusted under 35 U.S.C. 154(b) by 360 days.

(21) Appl. No.: 10/042,819

(22) Filed: Jan. 7, 2002

(65) Prior Publication Data

US 2003/0157488 A1 Aug. 21, 2003

(51) Int. Cl.[7] .......................... C12Q 1/68; C07H 21/02; C07H 21/04

(52) U.S. Cl. .......................... 435/6; 536/23.1; 536/24.3

(58) Field of Search .......................... 435/6; 536/23.1, 536/24.3

(56) References Cited

U.S. PATENT DOCUMENTS

| | | | |
|---|---|---|---|
| 5,445,934 A | 8/1995 | Fodor et al. | |
| 5,527,681 A | 6/1996 | Holmes | |
| 5,861,242 A | 1/1999 | Chee et al. | |
| 5,880,992 A | 3/1999 | Lee | |
| 5,972,614 A | * 10/1999 | Ruano et al. | |
| 6,027,880 A | 2/2000 | Cronin et al. | |
| 6,228,575 B1 | 5/2001 | Gingeras et al. | |

FOREIGN PATENT DOCUMENTS

| | | | |
|---|---|---|---|
| WO | WO0101218 A2 | * | 1/2001 |
| WO | WO0104270 A1 | * | 1/2001 |
| WO | 0180156 | | 10/2001 |

OTHER PUBLICATIONS

N. Patil, A. J. Berno, D. A. Hinds, W. A. Barrett, J. M. Doshi, C. R. Hacker, C. R. Kautzer, D. H. Lee, C. Marjoribanks, D. P. McDonough, B.T.N. Nguyen, M. C. Norris,J. B. Sheehan, N. Shen, D. Stem, R.P. Stokowski, D. J. Thomas, M. O. Trulson, K. R. Vyas, K. A. Frazer, S. P. A. Fodor, and D. R. Cox "Blocks of Limited Haplotype Diversity Revealed by High-Resolution Scanning of Human Chromosome 21" Science 294:1719–1723, (2001).

Slides from corporate presentation presented by Perlegen Sciences, Inc.

U.S. Ser. No. 60/327,006, filed Oct. 5, 2001, "Identifying Human SNP Haplotypes, Informative SNPs and Use Thereof," assigned to the assignee of the present invention (1005–P3, Incorporated herein by reference for all purposes).

Daly, M.J., Rioux, J.D., Schaffner, S.F., Hudson, T.J., Lander, E.S. High–resolution haplotype structure in the human genome Nature Genetics 29, 229–232, (2001).

Agarwal, P. et al. "Comparison study for identifying promoter allelic polymorphism in interleukin 10 and tumor necrosis factor alpha genes" Diagn Mol Pathol 9,158–64 (2000).

Cooksey, R.C., Holloway, B.P., Oldenburg, M.C., Listenbee, S. & Miller, C.W. "Evaluation of the Invader assay, a linear signal amplification method, for Identification of mutations associated with resistance to rifampin and isoniazid in *Mycobacterium tuberculosis*" Antimicrob Agents Chemother 44, 1296–301 (2000).

Griffin, T.J. & Smith, L.M. "Single–nucleotide polymorphism analysis by MALDI–TOF mass spectrometry" Trends Biotechnol 18, 77–84 (2000).

Griffin, T.J. & Smith, L.M. "Genetic identification by mass spectrometric analysis of single–nucleotide polymorphisms: ternary encoding of genotypes" Analytical Chemistry 72, 3298–3302 (2000).

Hall, J.G. et al. "Sensitive detection of DNA polymorphisms by the serial invasive signal amplification reaction" Proc Natl Acad Sci U S A 97, 8272–8277 (2000).

Hessner, M.J., Budish, M.A. & Friedman, K.D. "Genotyping of factor V G1691A (Leiden) without the use of PCR by Invasive cleavage of oligonucleotide probes" Clin Chem 46, 1051–6 (2000).

Ledford, M. et al. "A multi–site study for detection of the factor V (Leiden) mutation fromgenomic DNA using a homogeneous Invader microtiter plate FRET assay" J Molec Diagnostic 2, 97–104 (2000).

Lyamichev, V.I. et al. "Experimental and theoretical analysis of the invasive signal amplification reaction" Biochemistry 39, 9523–32 (2000).

Meln, C.A. et al. "Evaluation of single nucleotide polymorphism typing with invader on PCR amplicons and its automation" Ganome Res 10, 330–43 (2000).

Arnold, B.A., Hepler, R.W., and Keller, P.M. "One–Step Fluorescent Probe Production–Enhanced Reverse Transcriptase Assay" BioTechniques 25(1):98–106, (1998).

Becker K., D. Pan and C.B. Whitley, 1999. "Real–time quantitative polymerase chain reaction to assess gene transfer" Hum. Gene Ther. 10:2559–2566, (1999).

(Continued)

Primary Examiner—Ethan Whisenant
(74) Attorney, Agent, or Firm—Deana A. Arnold; Gulshan Shaver

(57) ABSTRACT

Improved systems and methods for performing genetic analyses. Full genomic DNA scans are performed on the genetic DNA from a plurality of individuals to identify genetic variants. For those variants, but not based on a full genetic DNA scan, the variants alone are scanned in additional individuals to identify blocks of the variants that tend to be inherited together.

26 Claims, 3 Drawing Sheets

OTHER PUBLICATIONS

Figure 1:
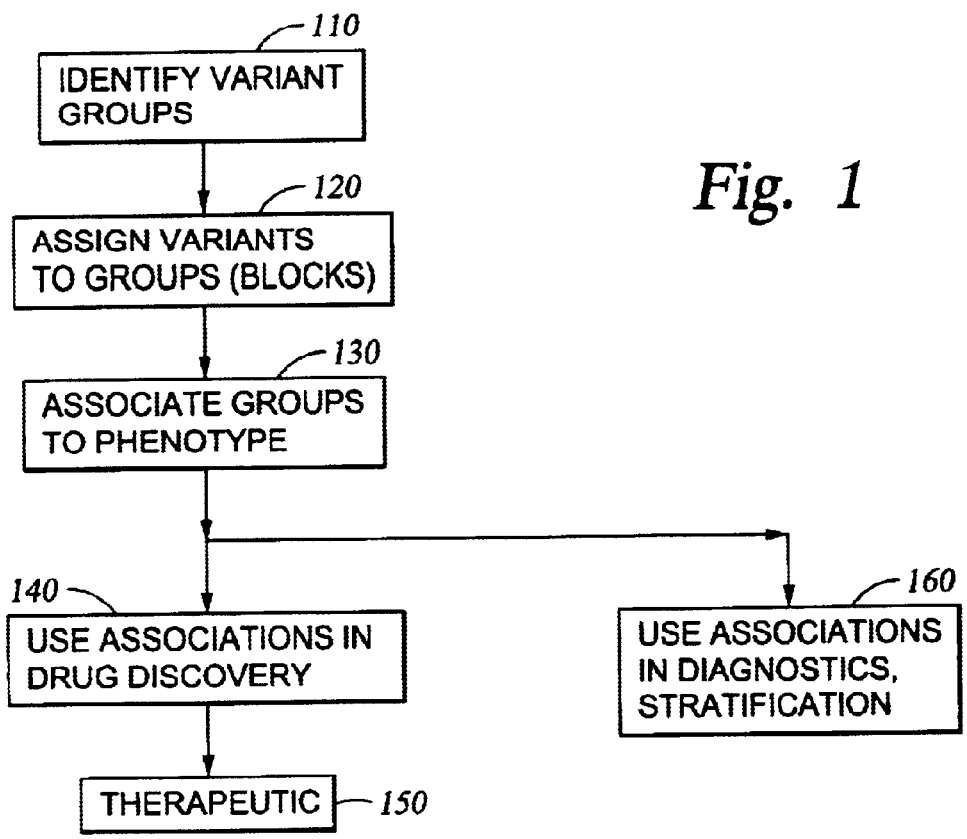

Berg, T., Miller, A.R., Platz, K.P., Hohne, M., Bechstein, W.O., Hopf, U., Wiedenmann, B., Neuhaus, P., and Schreier, E. "Dynamics of GB virus C viremia early after orthotopic liver transplantation Indicates extrahepatic tissues as the predominant site of GB virus C replication" *Hepatology* 29(1):245–249, (1999).

Judson R, Stephens JC. "The predictive power of haplotypes in clinical response" *Pharmacogenomics*. 1(1):15–26, (2000).

Drysdale, CM, McGraw DW, Stack CB, Stephens JC, Judson RS, Nandabalan K, Arnold K, Ruano G, Liggett SB "Complex promoter and coding region beta 2–adrenergic receptor haplotypes alter receptor expression and predict in vivo responsiveness" *Proc National Academy of Sciences U S A*. 97(19):10483–8, (2000).

Judson, R., Stephens, J.C., "Notes from the SNP vs. haplotype front" *Pharmacogenomics*. 2(1):1–7 (2001).

Oestreicher, P., "4th Annual Pharmacogenomics and Medicine Lectures" *Pharmacogenomics*. 2(3):291–296 (2001).

* cited by examiner

BLOCK: A CHROMOSOMAL REGION
WHICH TENDS TO BE INHERITED AS A UNIT,
WITH A SMALL NUMBER OF COMMON FORMS

|  | 241 | 242 | 243 | 244 | 245 | 246 | 247 | 248 | 249 | 250 | 251 | 252 | 253 |
|---|---|---|---|---|---|---|---|---|---|---|---|---|---|
| W | ...A... | G... | ...A | T... | T... | C... | G... | ...A | T... | A... | A... | C... | G |
| X | ...A... | G... | ...A | C... | T... | A... | C... | ...A | T... | A... | A... | C... | G |
| Y | ...T... | A... | ...T | T... | T... | C... | G... | ...A | T... | A... | A... | C... | G |
| Z | ...T... | A... | ...T | C... | T... | A... | C... | ...A | A... | T... | C... | A... | C |

SEQ ID NO:1
SEQ ID NO:2
SEQ ID NO:3
SEQ ID NO:4

261, 262, 263

*Fig. 2*

GENETIC ANALYSIS SYSTEMS AND METHODS

BACKGROUND OF THE INVENTION

The DNA that makes up human chromosomes provides the instructions that direct the production of all proteins in the body. These proteins carry out the vital functions of life. Variations in DNA often produce variations in the proteins, thus affecting the function of cells. Although environment often plays a significant role, variations or mutations in DNA are directly related to almost all human diseases, including infectious disease, cancer, inherited disorders, and autoimmune disorders. Moreover, knowledge of human genetics has led to the realization that many diseases result from either complex interactions of several genes or from any number of mutations within one gene. For example, Type I and II diabetes have been linked to multiple genes, each with its own pattern of mutations. In contrast, cystic fibrosis can be caused by any one of over 300 different mutations in a single gene.

Additionally, knowledge of human genetics has led to a limited understanding of differences between individuals when it comes to drug response—the field of pharmacogenetics. Since the first correlation over half a century ago of adverse drug responses with amino acid variations in two drug-metabolizing enzymes, plasma cholinesterase and glucose-6-phosphate dehydrogenase, careful genetic analyses have linked sequence polymorphisms in over 35 drug metabolism enzymes, 25 drug targets and 5 drug transporters with compromised levels of drug efficacy or safety. In the clinic, such information is being used to prevent drug toxicities; for example, patients are often screened for genetic differences in the thiopurine methyltransferase gene that cause decreased metabolism of 6-mercaptopurine or azathiopurine. Yet only a small percentage of observed drug toxicities have been explained adequately by the set of pharmacogenetic markers validated to date. In addition, insufficient therapeutic efficacy or unanticipated side effects in "outlier" individuals when administered drugs previously demonstrated to be both safe and efficacious in clinical trials is a tremendous problem for health care practitioners and presents a significant dilemma to the pharmaceutical industry.

Disease-related and pharmacogenetic gene validation relies on elements of population and quantitative genetics and robust statistical metrics; however, the first step normally relies upon identification of a candidate target gene. To date, various biotechnological methods have been employed to identify candidate genes. For example, differential gene expression has been employed, essentially looking for differences in gene expression between affected and unaffected individuals or between treated and untreated individuals. In addition, protein-protein interaction maps to identify drug receptors and their immediate effectors have been used. Another approach involves mining human sequence databases for sequences similar to accepted disease-related or pharmacokinetic or pharmacodynamic regulators.

Because any two humans are 99.9% similar in their genetic makeup, most of the sequence of the DNA of their genomes is identical. However, there are variations in DNA sequence between individuals. For example, there are deletions of many-base stretches of DNA, insertion of stretches of DNA, variations in the number of repetitive DNA elements in noncoding regions, and changes in single nitrogenous base positions in the genome called "single nucleotide polymorphisms" or "SNPs". It is estimated that there are 3 to 4 million common SNPs that occur in at least 10 percent of people. These common SNPs do not occur independently but are passed from generation to generation in variable-length blocks of multiple SNPs, forming patterns across the genome. Such blocks of SNPs are called SNP haplotype blocks herein.

The candidate gene identification strategy most relevant to SNPs is whole-genome association on various populations of individuals—that is, scanning the entire genomes of populations of individuals to correlate SNPs to disease or drug response. Such whole-genome analyses would provide a fine degree of genetic mapping and pinpoint specific regions of linkage. Methods have been proposed and are used in connection with whole genome analysis. For example, the methods described in U.S. Ser. No. 60/327,006, filed Oct. 5, 2001, "Identifying Human SNP Haplotypes, Informative SNPs and Uses Thereof," assigned to the assignee of the present invention, incorporated herein by reference for all purposes) have been proposed for use in such applications. U.S. Ser. No. 10/166,341, filed Sep. 18, 2001, "Human Genomic Polymorphisms", assigned to the assignee of the present invention incorporated herein by reference for all purposes, provides the identity of SNPs and SNP haplotype blocks across one representative chromosome, ie. Chromosome 21.

While meeting with success, it is desirable to increase the speed and efficiency at which such analyses can be performed, as well as to decrease the cost of performing such analyses.

SUMMARY OF THE INVENTION

Improved methods, devices, and systems for performing genetic analysis are provided. According to one embodiment of the invention a method is provided in which genetic DNA or derivatives therefrom is scanned from a plurality of individuals. The scanning uses, for example, a gel based sequencer or high density array to identify genetic polymorphisms in a plurality of individuals. For the polymorphisms that occur in a plurality of individuals, but not all of the scanned bases, genetic DNA or derivatives therefrom from additional individuals is evaluated to identify which of the variants occur in the additional individuals. Based the results of scanning the additional individuals, the method provides for the identification of blocks of the polymorphisms that tend to be inherited together. The blocks of polymorphisms can then be used in a wide variety of applications such as drug target identification, identification of diagnostics, clinical trial evaluation, pharmacogenomics, and other applications.

DETAILED DESCRIPTION OF THE PREFERRED EMBODIMENTS

Throughout the disclosure various patents, patent applications and publications are referenced. Unless otherwise indicated, each is incorporated by reference in its entirety for all purposes.

U.S. Ser. No. 60/327,006, filed Oct. 5, 2001, "Identifying Human SNP Haplotypes, Informative SNPs and Use Thereof," assigned to the assignee of the present invention incorporated herein by reference for all purposes, describes methods for identifying single nucleotide polymorphisms, assigning such polymorphisms to groups, and using such groups in the drug discovery process. FIG. 1 provides an overall diagram illustrating such processes. In FIG. 1, variant locations in a genome, such as the human genome, are identified in step 110. The processes used in step 110 can include, for example, scanning genomic regions for variants using DNA/RNA arrays such as those available from Affymetrix, Inc. (such as discussed in general in U.S. Pat. No. 5,861,242, incorporated herein by reference for all purposes), the use of conventional gel sequencing techniques such as those based on gel sequencers available from Applied Biosystems, Inc., capillary sequencing techniques, or other techniques. Preferably, only common SNPs, such as those that occur in more than 10% of the population in question, are used in the analysis since, for example, these SNPs will represent evolutionarily older variants and, therefore, tend to correlate with more common diseases/ states in a larger fraction of the population.

In preferred embodiments, the genomic DNA (or a derivative therefrom, such as PCR DNAs or RNA amplicons or the like) is scanned for variants using a high density DNA array. Using one technology, an array of probes is formed on a high density array. The array of probes includes a) probes that are complementary to portions of a baseline sequence of the genetic DNA (such as that obtained from a first pass sequencing effort) and b) one or more probes that are complementary to variants of the baseline sequence of the genetic DNA. The genetic DNA, or a derivative thereof, is then labeled and hybridized to the array and scanned. Based on the locations where hybridization is detected one can detect whether the bases in the genetic DNA are "wild type" or variant. In the cases where the particular base is the same as the reference sequence, the labeled material will hybridize more strongly to the wild type probe. In those cases where the DNA sequence varies from the reference sequence, the labeled material will hybridize more strongly to one of the variant probes. Based on this information, one can call a particular base as being the same or variant from the reference sequence.

In preferred embodiments, more than 10,000 bases are scanned for variants. In more preferred embodiments, more than $1 \times 10^6$ bases are scanned for variants, more preferably more than $2 \times 10^6$ bases, more preferably $1 \times 10^7$, and more preferably more than $1 \times 10^8$, and more preferably more than $1 \times 10^9$ bases are scanned for variants. In preferred embodiments at least introns are scanned for variants, and in more preferred embodiments both introns and exons are scanned for variants. In preferred embodiments the scanned nucleic acids are genomic DNA. In most preferred embodiments, such DNA is from a mammalian organism such as a human. In preferred embodiments, more than 10% of the genomic DNA from the organism is scanned, in more preferred embodiments more than 25% of the genomic DNA from the organism is scanned, in more preferred embodiments, more than 50% of the genomic DNA from the organism is scanned, and in most preferred embodiments, more than 75% of the genomic DNA is scanned.

In step 120 the variants are assigned to groups. Such groups of variants are blocks of variants (in most cases, single nucleotide polymorphisms or "SNPs") that tend to be inherited together. Such "blocks" or "SNP variant haplotype blocks" have likely arisen from an evolutionary point of view because the edges of blocks will tend to be the boundaries of ancient recombination events in the species. In step 130, representative variants from each block are used in an association study to identify associations of such blocks to a phenotype. Such association studies may be run using a variety of technologies such as a) Affymetrix genotyping arrays, b) "Invader" assays available from Third Wave, such as described in Agarwal, P. et al. "Comparison study for identifying promoter allelic polymorphism in interleukin 10 and tumor necrosis factor alpha genes", *Diagn Mol Pathol* 9, 158–64(2000); Cooksey, R. C., Holloway, B. P., Oldenburg, M. C., Listenbee, S. & Miller, C. W. "Evaluation of the Invader assay, a linear signal amplification method, for identification of mutations associated with resistance to rifampin and isoniazid in Mycobacterium tuberculosis" *Antimicrob Agents Chemother* 44, 1296–301 (2000); and Mein, C. A. et al. "Evaluation of single nucleotide polymorphism typing with Invader on PCR amplicons and its automation" *Genome Res* 10, 330–43 (2000), all incorporated herein by reference, or c) "Taqman" assays, such as described in Arnold, B. A., Hepler, R. W., and Keller, P. M. "One-Step Fluorescent Probe Product-Enhanced Reverse Transcriptase Assay" *BioTechniques* 25(1):98–106, 1998; Becker K., D. Pan and C. B. Whitley. 1999. Real-time quantitative polymerase chain reaction to assess gene transfer. Hum. Gene Ther. 10:2559–2566, 1999; Berg, T., Miller, A. R., Platz, K. P., Hohne, M., Bechstein, W. O., Hopf, U., Wiedenmann, B., Neuhaus, P., and Schreier, E. "Dynamics of GB virus C viremia early after orthotopic liver transplantation indicates extrahepatic tissues as the predominant site of GB virus C replication" *Hepatology* 29(1):245–249, 1999; or a variety of other technologies. When array based technologies are used, as an example, one makes arrays similar to those described above, except that only the variant positions are "tiled" onto the array.

Once it has been determined which regions of the genome are associated with, for example, a disease state, drug screening assays are run to identify one or more molecules that mediate the relevant portions of the genome in step 140 to identify therapeutics 150. In addition, the associations themselves may be used directly in genetic diagnostic assays, immunoassays or other diagnostic tests in step 160. In alternative embodiments the variant regions are used in studies to evaluate drug response such as in pharmacogenomic studies. The results are then used to stratify patents according to drug response. The stratification may, in some embodiments, be used to stratify individuals that may exhibit a toxic response from those that will not. In other cases, the stratification may separate those that will be non-responders from those who will be responders.

FIG. 2 provides one illustration of showing how variants, usually SNPs, occur in groups or blocks in a genome. Such SNP haplotype blocks are chromosomal regions that tend to be inherited as a unit, with a relatively small number of common forms. Each line in FIG. 2 represents portions of the haploid genome sequence of different individuals. As shown therein, individual W has an "A" at position 241, a "G" at position 242, and an "A" at position 243. Individual X has the same bases at positions 241, 242, and 243. Conversely, individual Y has a T at positions 241 and 243, but an A at position 242. Individual Z has the same bases as individual Y at positions 241, 242, and 243. The variants will most commonly be biallelic, ie. occur in only one of 2 forms, not all four possibilities. Variants in block 261 will tend to occur together. Similarly, the variants in blocks 262 and 263 will tend to occur together. Of course, only a few bases in a genome are shown in FIG. 2. In fact, most bases will be like those at position 245 and 248, and will not vary from individual to individual.

This tendency of SNPs to occur together in SNP haplotype blocks allows for a single or a few SNPs in a block to be used in an association study, rather than all of the SNPs in that block. For example, by evaluating only the SNP at position 241, the SNPs at positions 242 and 243 can be predicted without performing an assay to identify SNPs 242 and 243. If position 241 contains an A, position 242 will contain a G and position 243 will contain an A. Conversely, if position 241 contains a T, positions 242 and 243 respectively will contain an A and a T respectively. Similarly, a SNP in block 262 can be used to predict the other SNPs in block 262. For example, if SNP 244 is a T, it will be known that position 246 is a C, and position 247 is a G. Conversely, if position 244 is a C, position 246 is an A, and position 247 is a C.

According to the invention herein, all or substantially all of the bases in a genomic region are scanned for common SNPs in a first, limited, sample set. Then, using substantially only those SNPs identified in the first scanning step, additional individuals are genotyped at those SNP locations that are identified from a full scan of the genomic region of interest. The first sample set is sufficiently large that the full scan of genomic DNA identifies a sufficient number of SNPs with a sufficiently high level of confidence, but is not large enough to necessarily identify all of the block boundaries to a necessary level of confidence for the particular experiment. The second sample set is of a sufficient size that it will allow definition of block boundaries with a sufficient level of confidence for the experiment.

Figure 3:
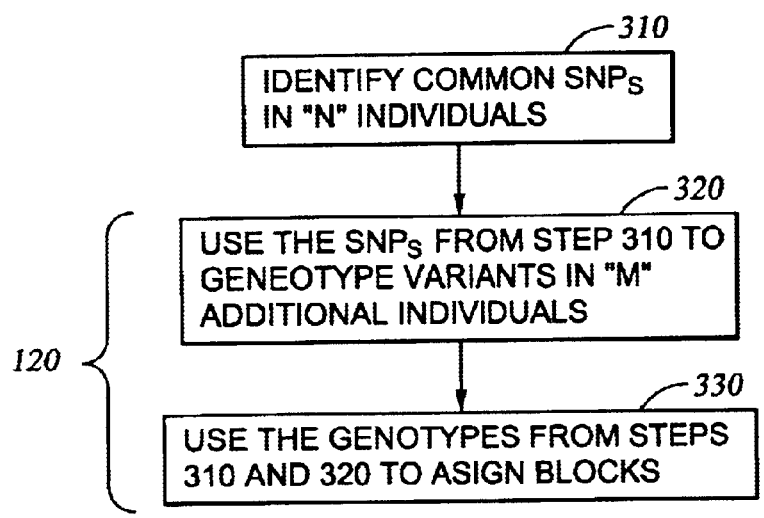

FIG. 3 illustrates the process in greater detail. As shown, at step 310 a subset of "n" genomic DNAs are scanned across all or a portion such genomes at every base location for common SNPs or variants. Thereafter, using genotyping technologies such as those described above, only those variant locations identified in step 310 are used to genotype an additional "m" individuals. Using the genotypes accumulated from steps 310 and 320, variant blocks are assigned. Using the invention herein, the cost and burden of performing genetic analysis, especially whole genome analysis, is significantly reduced since, for a fraction of the population analyzed, only a fraction of the bases of the genomic DNA of interest needs to be evaluated in assigning variants to respective blocks.

In preferred embodiments, copies of more than 10 different monoploid genomic DNAs are scanned for variants at step 310 to be used in the further genotyping analysis (i.e. "n" is 10 or more). In more preferred embodiments more than 15 different copies of the genomic DNA are scanned for variants to be used in the further genotyping analysis (i.e. "n" is 15 or more). In more preferred embodiments more than 18 copies of the genomic DNA are scanned for variants to be used in the further genotyping analysis (i.e. "n" is 18 or more). In more preferred embodiments more than 20 genomic DNAs are scanned for variants to be used in the further genotyping analysis (i.e. "n" is 20 or more). In more preferred embodiments more than 25 copies of the genomic DNA are scanned for variants to be used in the further genotyping analysis (i.e. "n" is 25 or more).

In preferred embodiments, the full scanning of genomic DNA is followed up by genotyping at step 320 of additional samples to evaluate representative SNPs discovered in the full scans. In preferred embodiments, the genotyping step 320 analyzes more than 10 different monoploid genomic DNAs (ie. "m" is 10 or more). In more preferred embodiments, the genotyping step 320 analyzes more than 15 different genomic DNAs. In more preferred embodiments, the genotyping step 320 analyzes more than 20 different genomic DNAs. In more preferred embodiments, the genotyping step 320 analyzes more than 25 different genomic DNAs. In more preferred embodiments, the genotyping step 320 analyzes more than 30 different genomic DNAs.

Figure 4:
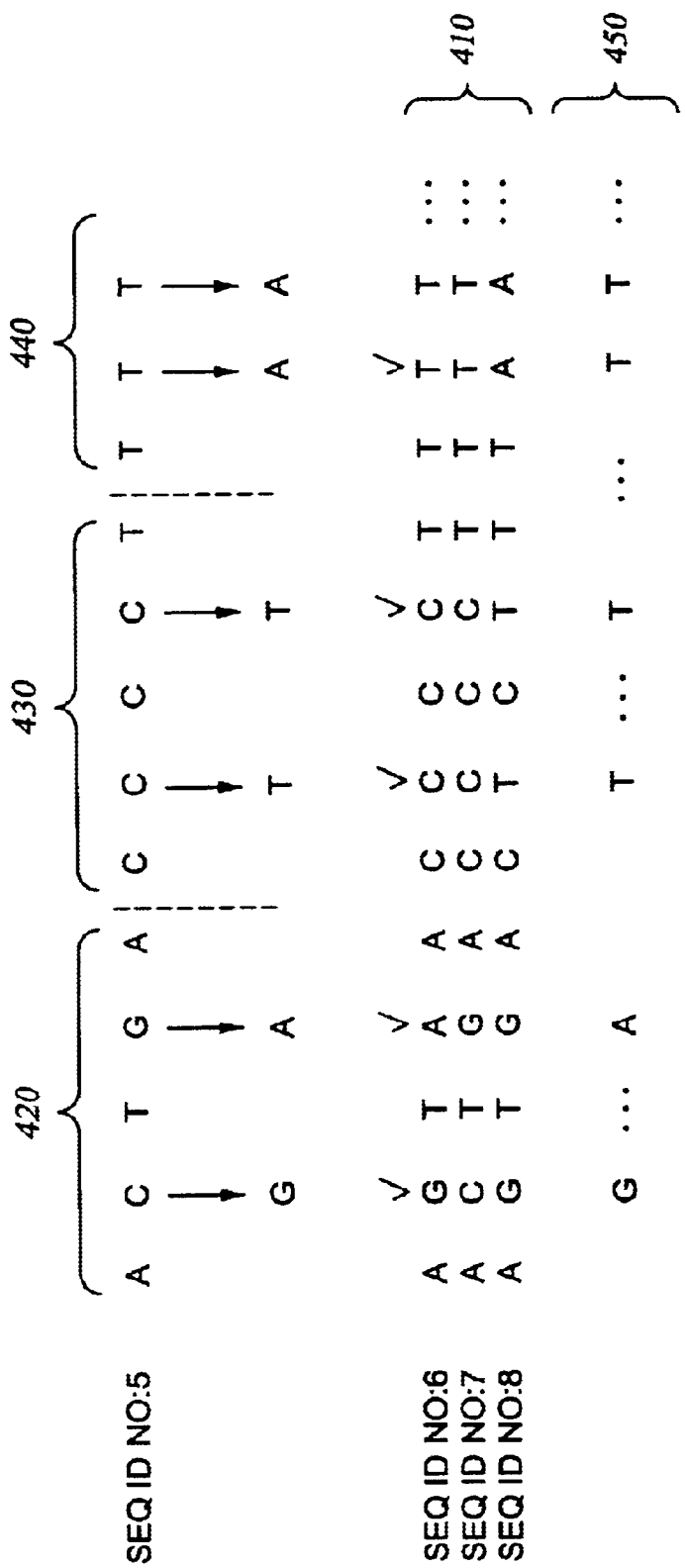

FIG. 4 illustrates the outcome of the process of FIG. 3 in a hypothetical situation. The top portion of FIG. 4 illustrates the sequence of a hypothetical stretch of DNA, with the variant positions indicated and variant block boundaries drawn. Of course, the top portion of FIG. 4 illustrates the stretch of genomic DNA with mutations marked and the block boundaries drawn, although this information would not be known ab initio. Sequencing results 410 show the results of sequencing haploid DNA of 3 individuals. As shown, in general it is possible to have identified a large fraction of the common SNPs after a relatively small number of individuals have been sequenced. In the case in FIG. 4, the SNPs at each location shown in the top portion of FIG. 4 have been identified, as indicated by check marks. However, if further individuals are not evaluated, the block boundaries would not be correctly identified at this stage. For example, while one could at this stage draw block boundaries between blocks 420 and 430 (note that the first C→G variant predicts the first G→A variant, and the first C→T variant predicts the second C→T variant), it is not possible to distinguish between the blocks 430 and 440 at this stage. At this stage it appears that the first C→T variant would predict the first and second T→A variants. Accordingly, a more statistically significant sample set is required to draw the block boundaries. However, since relevant SNPs have been identified, it is now possible to genotype only the variant positions to complete the process of identifying block boundaries without sequencing the entire stretch of genomic DNA.

The results of performing a genotyping process on only the SNPs in another hypothetical genomic sample are shown in FIG. 4 at 420. As shown, by performing this additional genotyping step, it is now possible to see that blocks 430 and 440 are distinguishable. Specifically, it is now possible to see that the first C→T variant does not track with the first and second T→A variants, but instead, the first C→T variant can be used to predict only the second C→T variant and the first T→A variant can be used only to predict the second T→A variant.

Without wishing to be bound by any particular theory of operation, it is believed that the basis on which the assays may be successfully utilized in this manner is found in the fact that a few individuals may be used to find the most common SNPs. The most common haplotypes account for most individuals, but less common haplotypes could be mis-ordered in terms of frequency of occurrence if a larger sample set is not used.

EXAMPLE(S)

Using Affymetrix whole wafers, a region of genomic DNA from chromosome 21 was scanned for polymorphic regions, generally using the methods of U.S. Ser. No. 60/327,006, filed Oct. 5, 2001, "Identifying Human SNP Haplotypes, Informative SNPs and Use Thereof," assigned to the assignee of the present invention, incorporated herein by reference for all purposes). 19 additional copies of chromosome 21 were then evaluated using the same techniques. "Common" SNPs were evaluated, meaning those that occur with an allele frequency of more than 10% in this particular example. To evaluate whether one may use 19 scans for SNP detection, rather than 38, it was determined how many SNPs would produce an allele frequency of >10% across all 38 scans, but are not considered common polymorphism in a set of just 19 scans. To have an allele frequency of >10% out of 38, a SNP would need to have a frequency of >20% in 19 scans, if it is not polymorphic at all in the other 19 scans. In the analysis performed, 89% of common SNPs were identified by evaluating just 19 scans. SNPs identified in the above analysis are shown in Tables 1, 2, and 3. Table 1 shows the SNPs that would have been found in both of the first and last 19 scans of a 38 scan set. Table 2 shows the SNPs that would have been identified by evaluating the first 19 of the 38 scans of chromosome 21, but would not have been identified by evaluating only the second 19 scans. Table 3 shows the SNPs that would have been identified by evaluating the last 19 of 38 scans of chromosome 21, but would not have been identified by evaluating only the first 19 scans. There are 3170 SNPs identified in both the first and last 19 scans. There are 361 SNPs found in only the first 19 scans, and 516 in only the second 19 scans. Therefore, there are $((0.5)*(361+516))/(3170+361+516)$ or 11% of the SNPs, on average, that would not be found in only half of the number of scans in chromosome 21.

TABLE 1

| | POSITION | REFERENCE_BASE | ALTERNATE_BASE |
|---|---|---|---|
| 1: | 13780263 | a | g |
| 2: | 13780367 | c | t |
| 3: | 13780384 | g | a |
| 4: | 13781532 | a | g |
| 5: | 13782288 | t | c |
| 6: | 13782368 | t | c |
| 7: | 13787259 | t | c |
| 8: | 13788521 | t | c |
| 9: | 13790624 | g | a |
| 10: | 13793189 | c | a |
| 11: | 13793483 | t | c |
| 12: | 13793851 | t | c |
| 13: | 13793902 | c | a |
| 14: | 13793923 | a | g |
| 15: | 13794104 | g | c |
| 16: | 13794163 | t | c |
| 17: | 13794309 | a | c |
| 18: | 13794556 | g | t |
| 19: | 13795184 | c | g |
| 20: | 13795310 | a | g |
| 21: | 13796245 | c | t |
| 22: | 13797171 | a | g |
| 23: | 13798473 | a | t |
| 24: | 13798594 | c | t |
| 25: | 13799031 | a | t |
| 26: | 13799116 | a | g |
| 27: | 13799679 | a | g |
| 28: | 13799935 | g | a |
| 29: | 13800043 | g | t |
| 30: | 13800201 | a | g |
| 31: | 13800956 | t | c |
| 32: | 13801272 | c | t |
| 33: | 13801560 | c | g |
| 34: | 13804651 | c | t |
| 35: | 13805013 | g | a |
| 36: | 13805107 | c | t |
| 37: | 13805416 | c | t |
| 38: | 13805691 | g | a |
| 39: | 13806436 | t | c |
| 40: | 13808142 | g | c |
| 41: | 13808771 | t | c |
| 42: | 13808776 | c | t |
| 43: | 13808906 | g | a |
| 44: | 13809243 | t | g |
| 45: | 13809448 | g | a |
| 46: | 13809729 | c | g |
| 47: | 13809964 | c | t |
| 48: | 13810532 | a | g |
| 49: | 13811589 | g | c |
| 50: | 13812436 | g | c |
| 51: | 13829193 | a | g |
| 52: | 13837787 | c | a |
| 53: | 13843201 | g | t |
| 54: | 13843560 | c | t |
| 55: | 13844156 | a | g |
| 56: | 13845008 | g | c |
| 57: | 13850206 | g | t |
| 58: | 13850467 | a | t |

TABLE 1-continued

| | POSITION | REFERENCE_BASE | ALTERNATE_BASE |
|---|---|---|---|
| 59: | 13850793 | g | c |
| 60: | 13851331 | g | a |
| 61: | 13851465 | t | c |
| 62: | 13851482 | g | a |
| 63: | 13851839 | a | t |
| 64: | 13853325 | t | g |
| 65: | 13854406 | t | c |
| 66: | 13855468 | g | a |
| 67: | 13857664 | g | a |
| 68: | 13859884 | g | c |
| 69: | 13861361 | t | c |
| 70: | 13862014 | g | c |
| 71: | 13862811 | a | c |
| 72: | 13864035 | c | t |
| 73: | 13864454 | g | t |
| 74: | 13865342 | c | t |
| 75: | 13869013 | c | t |
| 76: | 13870959 | a | t |
| 77: | 13870981 | a | g |
| 78: | 13872382 | a | g |
| 79: | 13872723 | a | t |
| 80: | 13874188 | a | g |
| 81: | 13875913 | a | g |
| 82: | 13876910 | a | g |
| 83: | 13877368 | t | a |
| 84: | 13877712 | g | a |
| 85: | 13877854 | t | c |
| 86: | 13880011 | c | t |
| 87: | 13880770 | g | a |
| 88: | 13883076 | c | t |
| 89: | 13883341 | t | g |
| 90: | 13883511 | a | g |
| 91: | 13883719 | c | t |
| 92: | 13884172 | g | a |
| 93: | 13884439 | a | g |
| 94: | 13884476 | c | t |
| 95: | 13885037 | c | t |
| 96: | 13888038 | a | t |
| 97: | 13888604 | g | t |
| 98: | 13889436 | t | c |
| 99: | 13890344 | g | a |
| 100: | 13890511 | g | a |
| 101: | 13891102 | a | t |
| 102: | 13891894 | a | g |
| 103: | 13891974 | g | a |
| 104: | 13892019 | t | c |
| 105: | 13892406 | a | t |
| 106: | 13892423 | a | g |
| 107: | 13892460 | c | a |
| 108: | 13892533 | c | t |
| 109: | 13892640 | t | c |
| 110: | 13894072 | g | a |
| 111: | 13894132 | c | a |
| 112: | 13894680 | a | g |
| 113: | 13895433 | g | a |
| 114: | 13901024 | t | g |
| 115: | 13902432 | t | g |
| 116: | 13903639 | c | g |
| 117: | 13904140 | g | a |
| 118: | 13905359 | c | t |
| 119: | 13906874 | a | g |
| 120: | 13908702 | t | g |
| 121: | 13923816 | a | g |
| 122: | 13924410 | g | c |
| 123: | 13928582 | g | a |
| 124: | 13929428 | g | a |
| 125: | 13932906 | g | a |
| 126: | 13934231 | a | c |
| 127: | 13934282 | t | c |
| 128: | 13934468 | t | c |
| 129: | 13934480 | a | c |
| 130: | 13934691 | t | c |
| 131: | 13936168 | t | c |
| 132: | 13939719 | g | t |
| 133: | 13945313 | g | c |
| 134: | 13945619 | t | c |
| 135: | 13946328 | t | c |

TABLE 1-continued

| POSITION | REFERENCE_BASE | ALTERNATE_BASE |
|---|---|---|
| 136: 13948558 | t | c |
| 137: 13957861 | t | c |
| 138: 13957897 | a | g |
| 139: 13961188 | t | c |
| 140: 13961398 | a | c |
| 141: 13963166 | t | a |
| 142: 13963226 | a | g |
| 143: 13964526 | t | g |
| 144: 13965988 | a | c |
| 145: 13967031 | a | g |
| 146: 13967361 | a | c |
| 147: 13968052 | c | g |
| 148: 13968186 | a | g |
| 149: 13968704 | t | g |
| 150: 13968772 | g | a |
| 151: 13969447 | c | g |
| 152: 13969802 | t | g |
| 153: 13969816 | t | a |
| 154: 13969885 | g | a |
| 155: 13969965 | a | c |
| 156: 13970342 | t | c |
| 157: 13971387 | t | a |
| 158: 13971823 | c | t |
| 159: 13983563 | g | a |
| 160: 13985003 | a | g |
| 161: 13985280 | t | g |
| 162: 13985454 | g | a |
| 163: 13985887 | a | c |
| 164: 13986661 | t | c |
| 165: 13987607 | a | g |
| 166: 13988282 | c | t |
| 167: 13989518 | t | c |
| 168: 13989987 | c | t |
| 169: 13991021 | c | a |
| 170: 13991140 | a | g |
| 171: 13991288 | a | g |
| 172: 13992670 | t | c |
| 173: 13992705 | c | t |
| 174: 13994022 | c | t |
| 175: 13996917 | t | c |
| 176: 13997836 | g | c |
| 177: 13998686 | t | a |
| 178: 13998835 | g | a |
| 179: 13999356 | t | a |
| 180: 14018678 | a | c |
| 181: 14018887 | t | g |
| 182: 14019896 | c | t |
| 183: 14024121 | g | a |
| 184: 14024187 | a | t |
| 185: 14024852 | c | g |
| 186: 14024923 | a | t |
| 187: 14028090 | g | a |
| 188: 14028399 | c | t |
| 189: 14028430 | g | a |
| 190: 14029873 | g | a |
| 191: 14031210 | g | t |
| 192: 14032972 | c | t |
| 193: 14033384 | t | a |
| 194: 14034385 | g | a |
| 195: 14038441 | g | c |
| 196: 14038480 | a | g |
| 197: 14038639 | t | c |
| 198: 14040439 | c | g |
| 199: 14040876 | g | a |
| 200: 14041428 | c | t |
| 201: 14041932 | a | g |
| 202: 14043266 | c | t |
| 203: 14044634 | a | g |
| 204: 14045104 | a | g |
| 205: 14045200 | a | g |
| 206: 14048027 | c | t |
| 207: 14048350 | c | t |
| 208: 14049343 | g | a |
| 209: 14050138 | g | a |
| 210: 14050258 | g | a |
| 211: 14051897 | c | t |
| 212: 14052199 | c | t |
| 213: 14053863 | a | g |
| 214: 14055606 | g | t |
| 215: 14055656 | a | g |
| 216: 14056221 | a | g |
| 217: 14056375 | g | a |
| 218: 14056470 | c | t |
| 219: 14057430 | t | c |
| 220: 14059144 | c | t |
| 221: 14060584 | t | c |
| 222: 14060804 | g | c |
| 223: 14061225 | c | t |
| 224: 14064737 | t | a |
| 225: 14067569 | a | g |
| 226: 14068069 | a | t |
| 227: 14068127 | t | g |
| 228: 14069638 | t | c |
| 229: 14070973 | t | c |
| 230: 14072067 | a | t |
| 231: 14078398 | g | a |
| 232: 14079489 | c | t |
| 233: 14080941 | a | c |
| 234: 14082287 | g | a |
| 235: 14082513 | a | g |
| 236: 14083192 | t | g |
| 237: 14083520 | t | c |
| 238: 14087424 | t | a |
| 239: 14087441 | g | a |
| 240: 14088548 | g | a |
| 241: 14091100 | c | g |
| 242: 14092256 | c | t |
| 243: 14093151 | c | g |
| 244: 14094373 | t | c |
| 245: 14096443 | g | t |
| 246: 14097696 | g | a |
| 247: 14098656 | a | c |
| 248: 14101014 | g | t |
| 249: 14102964 | g | a |
| 250: 14105489 | a | g |
| 251: 14105717 | c | t |
| 252: 14106349 | t | g |
| 253: 14106571 | t | c |
| 254: 14106827 | g | a |
| 255: 14106974 | t | c |
| 256: 14108664 | c | t |
| 257: 14108889 | c | g |
| 258: 14109194 | c | t |
| 259: 14109540 | a | g |
| 260: 14109875 | a | g |
| 261: 14109953 | t | c |
| 262: 14109982 | t | c |
| 263: 14110042 | c | t |
| 264: 14110270 | c | t |
| 265: 14110383 | t | c |
| 266: 14110462 | c | t |
| 267: 14110527 | c | a |
| 268: 14112293 | t | g |
| 269: 14112571 | c | t |
| 270: 14114928 | c | t |
| 271: 14115291 | a | g |
| 272: 14116560 | g | a |
| 273: 14117021 | a | g |
| 274: 14117699 | g | c |
| 275: 14117814 | a | g |
| 276: 14118003 | a | g |
| 277: 14118769 | t | c |
| 278: 14121320 | a | g |
| 279: 14121579 | t | c |
| 280: 14121866 | t | g |
| 281: 14122772 | t | c |
| 282: 14122865 | a | g |
| 283: 14124291 | a | g |
| 284: 14124472 | c | t |
| 285: 14124593 | g | c |
| 286: 14125680 | t | c |
| 287: 14129043 | a | g |
| 288: 14129176 | c | g |
| 289: 14130516 | g | a |

TABLE 1-continued

| | POSITION | REFERENCE_BASE | ALTERNATE_BASE |
|---|---|---|---|
| 290: | 14130838 | t | c |
| 291: | 14131390 | a | c |
| 292: | 14131972 | c | t |
| 293: | 14132126 | t | c |
| 294: | 14132401 | a | g |
| 295: | 14134814 | t | c |
| 296: | 14135469 | a | g |
| 297: | 14136092 | a | c |
| 298: | 14136237 | a | g |
| 299: | 14136296 | c | t |
| 300: | 14136795 | t | c |
| 301: | 14136889 | a | g |
| 302: | 14137167 | c | t |
| 303: | 14137397 | a | g |
| 304: | 14137990 | g | a |
| 305: | 14138306 | g | a |
| 306: | 14140410 | t | c |
| 307: | 14140637 | g | a |
| 308: | 14140847 | a | g |
| 309: | 14140940 | c | t |
| 310: | 14142190 | c | t |
| 311: | 14143299 | g | a |
| 312: | 14148398 | t | c |
| 313: | 14148765 | a | t |
| 314: | 14149402 | g | c |
| 315: | 14150692 | t | c |
| 316: | 14150844 | c | t |
| 317: | 14151614 | t | c |
| 318: | 14151757 | t | a |
| 319: | 14152283 | c | a |
| 320: | 14152410 | c | a |
| 321: | 14152443 | a | g |
| 322: | 14152519 | a | g |
| 323: | 14153887 | t | g |
| 324: | 14154251 | g | t |
| 325: | 14154271 | a | g |
| 326: | 14154689 | a | g |
| 327: | 14154783 | t | c |
| 328: | 14154976 | a | t |
| 329: | 14155259 | c | t |
| 330: | 14155374 | c | t |
| 331: | 14155524 | c | g |
| 332: | 14155638 | g | a |
| 333: | 14156729 | c | t |
| 334: | 14157020 | g | a |
| 335: | 14157103 | a | g |
| 336: | 14158286 | t | c |
| 337: | 14162213 | g | c |
| 338: | 14164467 | c | t |
| 339: | 14166866 | a | c |
| 340: | 14167915 | g | a |
| 341: | 14170156 | g | a |
| 342: | 14173042 | a | g |
| 343: | 14173477 | c | t |
| 344: | 14174757 | t | c |
| 345: | 14176517 | c | t |
| 346: | 14176757 | t | c |
| 347: | 14176972 | g | a |
| 348: | 14177117 | g | a |
| 349: | 14181577 | g | a |
| 350: | 14182229 | c | t |
| 351: | 14182354 | g | t |
| 352: | 14184334 | g | a |
| 353: | 14184808 | g | a |
| 354: | 14185989 | t | c |
| 355: | 14186027 | a | g |
| 356: | 14188115 | a | g |
| 357: | 14190855 | t | g |
| 358: | 14192479 | a | g |
| 359: | 14193521 | t | c |
| 360: | 14194389 | g | a |
| 361: | 14198173 | c | t |
| 362: | 14201219 | a | g |
| 363: | 14202630 | t | c |
| 364: | 14203012 | t | c |
| 365: | 14203271 | a | g |
| 366: | 14203553 | c | t |
| 367: | 14203777 | a | c |
| 368: | 14203951 | g | a |
| 369: | 14204809 | g | a |
| 370: | 14207361 | c | t |
| 371: | 14207605 | g | a |
| 372: | 14207771 | c | t |
| 373: | 14207834 | a | g |
| 374: | 14208286 | a | t |
| 375: | 14208359 | t | c |
| 376: | 14208434 | c | t |
| 377: | 14208530 | t | c |
| 378: | 14208685 | c | t |
| 379: | 14208750 | t | a |
| 380: | 14208793 | c | t |
| 381: | 14209006 | c | t |
| 382: | 14209020 | a | t |
| 383: | 14209282 | c | t |
| 384: | 14209654 | t | c |
| 385: | 14209703 | t | c |
| 386: | 14210273 | a | c |
| 387: | 14211548 | c | t |
| 388: | 14212470 | g | a |
| 389: | 14214548 | g | c |
| 390: | 14214851 | t | c |
| 391: | 14217859 | g | a |
| 392: | 14218529 | a | g |
| 393: | 14218614 | a | t |
| 394: | 14221089 | a | g |
| 395: | 14221164 | a | g |
| 396: | 14221292 | g | a |
| 397: | 14221430 | a | g |
| 398: | 14221732 | c | t |
| 399: | 14224920 | g | a |
| 400: | 14228269 | g | c |
| 401: | 14230621 | c | t |
| 402: | 14230681 | a | c |
| 403: | 14232644 | t | a |
| 404: | 14233411 | c | a |
| 405: | 14234037 | t | c |
| 406: | 14234266 | g | a |
| 407: | 14235064 | c | a |
| 408: | 14235204 | c | t |
| 409: | 14235402 | g | a |
| 410: | 14235813 | c | t |
| 411: | 14236459 | a | g |
| 412: | 14236901 | g | a |
| 413: | 14236906 | a | c |
| 414: | 14236958 | g | t |
| 415: | 14237106 | c | t |
| 416: | 14237734 | a | g |
| 417: | 14238131 | g | a |
| 418: | 14238784 | g | a |
| 419: | 14238979 | a | t |
| 420: | 14239101 | c | t |
| 421: | 14239346 | t | c |
| 422: | 14239458 | g | a |
| 423: | 14239594 | a | g |
| 424: | 14239790 | t | g |
| 425: | 14239876 | t | c |
| 426: | 14240218 | c | t |
| 427: | 14240377 | t | a |
| 428: | 14240473 | a | g |
| 429: | 14241088 | a | g |
| 430: | 14241702 | a | g |
| 431: | 14241849 | g | a |
| 432: | 14242333 | c | t |
| 433: | 14243007 | a | t |
| 434: | 14243211 | g | c |
| 435: | 14248044 | a | c |
| 436: | 14249184 | c | g |
| 437: | 14251286 | g | c |
| 438: | 14255172 | g | a |
| 439: | 14255802 | c | a |
| 440: | 14258178 | c | t |
| 441: | 14259060 | g | a |
| 442: | 14259161 | c | t |
| 443: | 14265514 | a | g |

TABLE 1-continued

| | POSITION | REFERENCE_BASE | ALTERNATE_BASE |
|---|---|---|---|
| 444: | 14266004 | g | c |
| 445: | 14266784 | a | g |
| 446: | 14270911 | c | t |
| 447: | 14271868 | t | c |
| 448: | 14273519 | a | t |
| 449: | 14275793 | c | a |
| 450: | 14275916 | g | a |
| 451: | 14276093 | t | c |
| 452: | 14276177 | a | g |
| 453: | 14276528 | g | a |
| 454: | 14276897 | g | a |
| 455: | 14276972 | t | c |
| 456: | 14278155 | a | g |
| 457: | 14278615 | a | g |
| 458: | 14278692 | g | a |
| 459: | 14279892 | g | a |
| 460: | 14280148 | g | a |
| 461: | 14280291 | a | g |
| 462: | 14280782 | c | t |
| 463: | 14281042 | a | c |
| 464: | 14283354 | t | c |
| 465: | 14290678 | t | c |
| 466: | 14290844 | a | g |
| 467: | 14295679 | c | t |
| 468: | 14297092 | g | a |
| 469: | 14300848 | t | c |
| 470: | 14303184 | t | c |
| 471: | 14303913 | a | g |
| 472: | 14303970 | g | a |
| 473: | 14304669 | c | g |
| 474: | 14305073 | t | c |
| 475: | 14305360 | t | c |
| 476: | 14307893 | t | c |
| 477: | 14308069 | c | t |
| 478: | 14308329 | a | c |
| 479: | 14308625 | t | c |
| 480: | 14309321 | g | a |
| 481: | 14309465 | g | c |
| 482: | 14310218 | g | a |
| 483: | 14310672 | t | c |
| 484: | 14311035 | a | g |
| 485: | 14311228 | t | c |
| 486: | 14311491 | g | a |
| 487: | 14311865 | c | t |
| 488: | 14312093 | a | t |
| 489: | 14312165 | g | t |
| 490: | 14312256 | a | g |
| 491: | 14312275 | t | c |
| 492: | 14312321 | a | t |
| 493: | 14312797 | g | a |
| 494: | 14313371 | t | c |
| 495: | 14313671 | c | t |
| 496: | 14313711 | g | a |
| 497: | 14315626 | c | t |
| 498: | 14317417 | g | a |
| 499: | 14317572 | t | c |
| 500: | 14317812 | c | g |
| 501: | 14318978 | t | a |
| 502: | 14319024 | a | g |
| 503: | 14319433 | g | a |
| 504: | 14319634 | g | a |
| 505: | 14319797 | c | g |
| 506: | 14320165 | a | g |
| 507: | 14320692 | c | a |
| 508: | 14320813 | c | t |
| 509: | 14320844 | t | g |
| 510: | 14321619 | a | g |
| 511: | 14322052 | a | g |
| 512: | 14322154 | a | g |
| 513: | 14322220 | a | g |
| 514: | 14323488 | c | t |
| 515: | 14323680 | c | t |
| 516: | 14323863 | c | a |
| 517: | 14323972 | t | c |
| 518: | 14324040 | a | t |
| 519: | 14325197 | a | g |
| 520: | 14325540 | a | g |
| 521: | 14329541 | t | c |
| 522: | 14331105 | c | t |
| 523: | 14338523 | a | c |
| 524: | 14339636 | g | c |
| 525: | 14340427 | c | t |
| 526: | 14348472 | g | a |
| 527: | 14350385 | c | t |
| 528: | 14350727 | g | a |
| 529: | 14351732 | t | g |
| 530: | 14351887 | g | a |
| 531: | 14352733 | c | t |
| 532: | 14353465 | a | g |
| 533: | 14353545 | t | c |
| 534: | 14354282 | t | a |
| 535: | 14354993 | t | c |
| 536: | 14355347 | c | t |
| 537: | 14355495 | c | a |
| 538: | 14356310 | g | a |
| 539: | 14357040 | a | g |
| 540: | 14357331 | g | a |
| 541: | 14359127 | g | a |
| 542: | 14363514 | g | a |
| 543: | 14367075 | c | t |
| 544: | 14368787 | g | t |
| 545: | 14373239 | t | c |
| 546: | 14373986 | t | g |
| 547: | 14375753 | t | c |
| 548: | 14375760 | g | a |
| 549: | 14375831 | a | c |
| 550: | 14376454 | c | g |
| 551: | 14376567 | g | a |
| 552: | 14376808 | t | a |
| 553: | 14377209 | g | a |
| 554: | 14377288 | g | a |
| 555: | 14377353 | g | t |
| 556: | 14378276 | g | a |
| 557: | 14378370 | c | t |
| 558: | 14379197 | a | g |
| 559: | 14395036 | a | c |
| 560: | 14395259 | g | a |
| 561: | 14395598 | a | g |
| 562: | 14395625 | c | t |
| 563: | 14395690 | t | g |
| 564: | 14395722 | t | c |
| 565: | 14395818 | g | c |
| 566: | 14395870 | t | c |
| 567: | 14395902 | a | t |
| 568: | 14395954 | g | a |
| 569: | 14396424 | g | a |
| 570: | 14397242 | t | c |
| 571: | 14397529 | c | t |
| 572: | 14398288 | t | g |
| 573: | 14398896 | g | c |
| 574: | 14399028 | c | t |
| 575: | 14399757 | a | g |
| 576: | 14399925 | t | g |
| 577: | 14400367 | c | a |
| 578: | 14400745 | g | a |
| 579: | 14401434 | a | c |
| 580: | 14401454 | g | a |
| 581: | 14402273 | c | a |
| 582: | 14402935 | t | c |
| 583: | 14403897 | g | c |
| 584: | 14405247 | c | a |
| 585: | 14405732 | c | t |
| 586: | 14407060 | a | t |
| 587: | 14407160 | t | c |
| 588: | 14412731 | g | a |
| 589: | 14413737 | c | a |
| 590: | 14414482 | c | t |
| 591: | 14414726 | g | a |
| 592: | 14417171 | t | c |
| 593: | 14417396 | c | a |
| 594: | 14417433 | g | t |
| 595: | 14417477 | c | t |
| 596: | 14418160 | c | t |
| 597: | 14419575 | t | c |

TABLE 1-continued

| | POSITION | REFERENCE_BASE | ALTERNATE_BASE |
|---|---|---|---|
| 598: | 14420742 | t | c |
| 599: | 14421092 | a | g |
| 600: | 14421138 | t | g |
| 601: | 14422812 | a | t |
| 602: | 14424569 | g | a |
| 603: | 14424712 | t | g |
| 604: | 14427528 | g | a |
| 605: | 14434249 | a | g |
| 606: | 14434697 | g | a |
| 607: | 14437186 | t | c |
| 608: | 14437221 | t | g |
| 609: | 14438332 | t | c |
| 610: | 14438364 | t | g |
| 611: | 14438686 | t | c |
| 612: | 14438954 | g | a |
| 613: | 14439018 | t | c |
| 614: | 14439260 | t | c |
| 615: | 14440001 | c | t |
| 616: | 14443243 | c | t |
| 617: | 14446477 | c | t |
| 618: | 14447783 | g | a |
| 619: | 14447829 | t | a |
| 620: | 14448561 | c | g |
| 621: | 14449993 | c | a |
| 622: | 14453820 | a | g |
| 623: | 14455156 | c | t |
| 624: | 14458430 | g | a |
| 625: | 14462774 | a | c |
| 626: | 14464432 | g | c |
| 627: | 14465972 | t | c |
| 628: | 14466544 | a | c |
| 629: | 14466865 | a | g |
| 630: | 14477623 | g | t |
| 631: | 14479073 | t | a |
| 632: | 14479413 | a | g |
| 633: | 14483845 | c | t |
| 634: | 14484193 | t | c |
| 635: | 14485018 | t | c |
| 636: | 14500633 | a | g |
| 637: | 14501053 | a | g |
| 638: | 14501214 | g | t |
| 639: | 14505546 | c | t |
| 640: | 14507257 | c | t |
| 641: | 14507719 | a | g |
| 642: | 14507822 | c | g |
| 643: | 14508413 | a | t |
| 644: | 14508697 | g | a |
| 645: | 14509951 | c | t |
| 646: | 14511271 | c | t |
| 647: | 14512196 | g | a |
| 648: | 14513266 | t | c |
| 649: | 14514848 | c | t |
| 650: | 14516734 | c | t |
| 651: | 14517397 | c | t |
| 652: | 14517691 | t | c |
| 653: | 14519222 | c | t |
| 654: | 14519896 | c | t |
| 655: | 14525005 | g | c |
| 656: | 14528986 | g | c |
| 657: | 14529523 | g | c |
| 658: | 14530483 | t | c |
| 659: | 14531846 | c | a |
| 660: | 14532854 | g | a |
| 661: | 14534505 | c | a |
| 662: | 14535097 | g | a |
| 663: | 14539337 | g | c |
| 664: | 14540886 | g | a |
| 665: | 14542312 | t | c |
| 666: | 14545961 | g | c |
| 667: | 14546904 | t | c |
| 668: | 14546926 | g | a |
| 669: | 14549011 | g | a |
| 670: | 14556845 | g | t |
| 671: | 14558860 | a | g |
| 672: | 14560480 | a | g |
| 673: | 14561574 | c | t |
| 674: | 14573065 | a | c |
| 675: | 14574488 | a | g |
| 676: | 14574929 | t | a |
| 677: | 14581074 | g | a |
| 678: | 14586576 | c | g |
| 679: | 14588231 | g | t |
| 680: | 14588677 | a | t |
| 681: | 14591087 | a | t |
| 682: | 14594493 | c | t |
| 683: | 14598453 | c | g |
| 684: | 14600129 | c | t |
| 685: | 14601491 | g | c |
| 686: | 14603502 | g | a |
| 687: | 14603668 | t | a |
| 688: | 14609395 | t | c |
| 689: | 14610858 | g | a |
| 690: | 14615168 | t | c |
| 691: | 14615291 | a | g |
| 692: | 14616327 | g | a |
| 693: | 14618602 | g | a |
| 694: | 14618604 | g | a |
| 695: | 14618892 | c | t |
| 696: | 14619088 | g | a |
| 697: | 14621021 | t | c |
| 698: | 14621080 | a | g |
| 699: | 14621596 | c | a |
| 700: | 14626694 | g | a |
| 701: | 14627326 | t | c |
| 702: | 14627496 | t | c |
| 703: | 14627573 | g | a |
| 704: | 14627856 | c | t |
| 705: | 14628410 | a | c |
| 706: | 14628606 | t | c |
| 707: | 14628943 | g | t |
| 708: | 14630897 | a | g |
| 709: | 14631416 | c | a |
| 710: | 14631564 | t | c |
| 711: | 14631874 | c | g |
| 712: | 14632569 | c | t |
| 713: | 14633168 | g | t |
| 714: | 14633809 | t | c |
| 715: | 14635240 | t | g |
| 716: | 14637360 | a | g |
| 717: | 14637499 | a | t |
| 718: | 14638334 | a | g |
| 719: | 14638554 | g | a |
| 720: | 14638696 | t | c |
| 721: | 14639083 | g | a |
| 722: | 14639418 | c | t |
| 723: | 14639424 | t | a |
| 724: | 14640672 | g | c |
| 725: | 14640709 | g | c |
| 726: | 14640930 | a | c |
| 727: | 14640953 | a | g |
| 728: | 14641901 | a | g |
| 729: | 14641976 | g | a |
| 730: | 14642051 | c | t |
| 731: | 14642174 | g | a |
| 732: | 14642247 | t | a |
| 733: | 14642286 | a | g |
| 734: | 14642392 | t | c |
| 735: | 14642614 | c | t |
| 736: | 14642775 | a | c |
| 737: | 14642852 | c | t |
| 738: | 14644032 | c | g |
| 739: | 14644292 | c | t |
| 740: | 14644589 | c | a |
| 741: | 14644653 | g | a |
| 742: | 14645037 | c | t |
| 743: | 14645885 | c | g |
| 744: | 14646291 | c | t |
| 745: | 14646415 | g | a |
| 746: | 14647137 | c | t |
| 747: | 14649329 | g | a |
| 748: | 14649396 | t | c |
| 749: | 14649442 | g | a |
| 750: | 14649469 | a | g |
| 751: | 14649532 | a | c |

TABLE 1-continued

| | POSITION | REFERENCE_BASE | ALTERNATE_BASE |
|---|---|---|---|
| 752: | 14649566 | t | c |
| 753: | 14649661 | c | t |
| 754: | 14649855 | t | c |
| 755: | 14650183 | t | c |
| 756: | 14650197 | g | a |
| 757: | 14650588 | a | g |
| 758: | 14650730 | g | a |
| 759: | 14650852 | g | c |
| 760: | 14651277 | g | t |
| 761: | 14651335 | a | g |
| 762: | 14651435 | t | c |
| 763: | 14651847 | c | t |
| 764: | 14652004 | g | a |
| 765: | 14652162 | c | t |
| 766: | 14652276 | a | g |
| 767: | 14652452 | t | c |
| 768: | 14652474 | c | t |
| 769: | 14652694 | g | a |
| 770: | 14653708 | t | c |
| 771: | 14654235 | a | g |
| 772: | 14661002 | a | g |
| 773: | 14662594 | g | a |
| 774: | 14663947 | a | g |
| 775: | 14664293 | t | c |
| 776: | 14667946 | a | g |
| 777: | 14668382 | c | g |
| 778: | 14677906 | a | g |
| 779: | 14677931 | g | t |
| 780: | 14683355 | a | g |
| 781: | 14683707 | a | g |
| 782: | 14683953 | g | c |
| 783: | 14685321 | t | c |
| 784: | 14685566 | g | a |
| 785: | 14685682 | g | a |
| 786: | 14685868 | a | g |
| 787: | 14686114 | a | g |
| 788: | 14686396 | t | c |
| 789: | 14686751 | c | t |
| 790: | 14686876 | c | t |
| 791: | 14687010 | g | a |
| 792: | 14687213 | a | t |
| 793: | 14689122 | t | c |
| 794: | 14689887 | a | c |
| 795: | 14690010 | g | a |
| 796: | 14690527 | c | t |
| 797: | 14690707 | t | c |
| 798: | 14693607 | g | a |
| 799: | 14694039 | t | c |
| 800: | 14694137 | t | c |
| 801: | 14694226 | a | g |
| 802: | 14695601 | a | g |
| 803: | 14697255 | t | c |
| 804: | 14697625 | t | c |
| 805: | 14698201 | a | g |
| 806: | 14702430 | a | g |
| 807: | 14703794 | t | g |
| 808: | 14707050 | g | a |
| 809: | 14708403 | g | a |
| 810: | 14709040 | c | a |
| 811: | 14713360 | t | c |
| 812: | 14713782 | c | t |
| 813: | 14715259 | t | g |
| 814: | 14715324 | t | c |
| 815: | 14715436 | c | t |
| 816: | 14715840 | t | a |
| 817: | 14716796 | t | a |
| 818: | 14716938 | t | a |
| 819: | 14717692 | a | t |
| 820: | 14720670 | t | g |
| 821: | 14720870 | a | g |
| 822: | 14720958 | a | g |
| 823: | 14721377 | g | t |
| 824: | 14721393 | c | g |
| 825: | 14723843 | g | c |
| 826: | 14724043 | c | t |
| 827: | 14724396 | a | g |
| 828: | 14735736 | c | t |
| 829: | 14746369 | g | a |
| 830: | 14747341 | c | t |
| 831: | 14747564 | t | c |
| 832: | 14749491 | g | t |
| 833: | 14751000 | g | a |
| 834: | 14752476 | a | g |
| 835: | 14755501 | g | a |
| 836: | 14757128 | a | t |
| 837: | 14758013 | a | g |
| 838: | 14760186 | a | g |
| 839: | 14761259 | t | c |
| 840: | 14761655 | a | g |
| 841: | 14761848 | c | t |
| 842: | 14762060 | c | t |
| 843: | 14762610 | c | t |
| 844: | 14763252 | a | g |
| 845: | 14763339 | t | g |
| 846: | 14763358 | c | t |
| 847: | 14764385 | c | t |
| 848: | 14764832 | g | a |
| 849: | 14766118 | c | t |
| 850: | 14766695 | c | g |
| 851: | 14767381 | c | t |
| 852: | 14767448 | g | t |
| 853: | 14767691 | g | t |
| 854: | 14768282 | a | c |
| 855: | 14768485 | a | g |
| 856: | 14769892 | c | t |
| 857: | 14775735 | g | t |
| 858: | 14778167 | a | g |
| 859: | 14778548 | g | a |
| 860: | 14780565 | g | a |
| 861: | 14782481 | c | t |
| 862: | 14783170 | t | c |
| 863: | 14783238 | g | a |
| 864: | 14783528 | c | t |
| 865: | 14789648 | g | c |
| 866: | 14789869 | a | g |
| 867: | 14792310 | a | g |
| 868: | 14793132 | a | g |
| 869: | 14793358 | c | t |
| 870: | 14794571 | c | t |
| 871: | 14794694 | g | a |
| 872: | 14795297 | g | c |
| 873: | 14795613 | t | g |
| 874: | 14800961 | c | t |
| 875: | 14801290 | a | g |
| 876: | 14806680 | c | t |
| 877: | 14806780 | g | t |
| 878: | 14808807 | g | a |
| 879: | 14812321 | c | t |
| 880: | 14815234 | t | g |
| 881: | 14815292 | a | g |
| 882: | 14826491 | g | a |
| 883: | 14826755 | g | c |
| 884: | 14827063 | t | g |
| 885: | 14827326 | g | a |
| 886: | 14828570 | a | t |
| 887: | 14828644 | t | a |
| 888: | 14830149 | c | t |
| 889: | 14830865 | c | a |
| 890: | 14832282 | t | c |
| 891: | 14837049 | t | g |
| 892: | 14837309 | t | g |
| 893: | 14839377 | a | g |
| 894: | 14839380 | c | g |
| 895: | 14839479 | c | a |
| 896: | 14840370 | a | g |
| 897: | 14841070 | a | g |
| 898: | 14841947 | g | c |
| 899: | 14844054 | c | a |
| 900: | 14844695 | g | t |
| 901: | 14847684 | g | a |
| 902: | 14856106 | a | c |
| 903: | 14856305 | g | c |
| 904: | 14881867 | c | a |
| 905: | 14881913 | c | g |

TABLE 1-continued

| | POSITION | REFERENCE_BASE | ALTERNATE_BASE |
|---|---|---|---|
| 906: | 14883268 | c | g |
| 907: | 14883463 | c | t |
| 908: | 14883496 | a | c |
| 909: | 14884123 | a | g |
| 910: | 14885200 | t | c |
| 911: | 14886115 | a | g |
| 912: | 14889393 | a | g |
| 913: | 14890241 | t | c |
| 914: | 14890955 | a | c |
| 915: | 14891235 | g | t |
| 916: | 14891547 | g | a |
| 917: | 14893013 | g | a |
| 918: | 14897516 | a | g |
| 919: | 14897784 | c | t |
| 920: | 14898476 | c | t |
| 921: | 14898703 | t | g |
| 922: | 14899985 | g | a |
| 923: | 14900173 | t | c |
| 924: | 14900736 | g | t |
| 925: | 14901418 | c | t |
| 926: | 14902815 | g | a |
| 927: | 14903113 | c | a |
| 928: | 14903529 | c | t |
| 929: | 14904378 | g | a |
| 930: | 14906025 | t | g |
| 931: | 14907342 | t | c |
| 932: | 14907394 | a | c |
| 933: | 14907419 | c | a |
| 934: | 14907479 | t | c |
| 935: | 14907742 | a | g |
| 936: | 14916208 | a | g |
| 937: | 14916813 | c | t |
| 938: | 14916928 | t | c |
| 939: | 14917091 | g | a |
| 940: | 14917492 | t | c |
| 941: | 14917583 | g | a |
| 942: | 14918606 | a | g |
| 943: | 14919603 | c | t |
| 944: | 14921284 | t | c |
| 945: | 14921968 | g | a |
| 946: | 14925699 | a | g |
| 947: | 14927086 | g | t |
| 948: | 14927511 | g | t |
| 949: | 14927761 | a | g |
| 950: | 14930449 | c | t |
| 951: | 14932928 | g | t |
| 952: | 14934064 | g | a |
| 953: | 14934220 | a | t |
| 954: | 14934405 | c | g |
| 955: | 14935053 | g | a |
| 956: | 14936874 | c | t |
| 957: | 14937239 | a | g |
| 958: | 14938600 | a | g |
| 959: | 14938812 | t | c |
| 960: | 14938839 | c | t |
| 961: | 14939511 | t | g |
| 962: | 14946414 | t | c |
| 963: | 14947066 | a | t |
| 964: | 14948931 | a | g |
| 965: | 14949714 | g | a |
| 966: | 14949860 | t | g |
| 967: | 14950617 | c | t |
| 968: | 14955687 | c | t |
| 969: | 14957284 | a | g |
| 970: | 14957361 | t | c |
| 971: | 14957636 | c | t |
| 972: | 14962229 | a | t |
| 973: | 14962364 | g | c |
| 974: | 14962869 | a | g |
| 975: | 14962889 | c | c |
| 976: | 14962958 | c | c |
| 977: | 14963125 | c | t |
| 978: | 14963174 | a | c |
| 979: | 14963729 | c | c |
| 980: | 14964357 | a | c |
| 981: | 14964447 | c | c |
| 982: | 14965500 | c | c |
| 983: | 14966506 | g | a |
| 984: | 14967947 | c | g |
| 985: | 14967998 | c | t |
| 986: | 14968368 | g | a |
| 987: | 14968428 | t | c |
| 988: | 14968442 | c | g |
| 989: | 14968847 | t | c |
| 990: | 14968966 | c | t |
| 991: | 14969157 | g | c |
| 992: | 14969298 | c | a |
| 993: | 14970379 | t | c |
| 994: | 14970418 | g | a |
| 995: | 14971526 | c | t |
| 996: | 14971688 | c | g |
| 997: | 14971772 | g | a |
| 998: | 14973076 | g | a |
| 999: | 14973499 | c | a |
| 1000: | 14973824 | g | c |
| 1001: | 14973949 | t | g |
| 1002: | 14974011 | t | c |
| 1003: | 14974148 | g | a |
| 1004: | 14974260 | t | c |
| 1005: | 14974378 | a | g |
| 1006: | 14974460 | t | c |
| 1007: | 14982560 | a | g |
| 1008: | 14983098 | a | c |
| 1009: | 14983702 | a | g |
| 1010: | 14984246 | g | t |
| 1011: | 14984593 | a | g |
| 1012: | 14984596 | c | t |
| 1013: | 14985092 | a | c |
| 1014: | 14985239 | t | c |
| 1015: | 14986242 | c | g |
| 1016: | 14986505 | t | g |
| 1017: | 14999579 | t | c |
| 1018: | 14999732 | t | c |
| 1019: | 15000805 | t | c |
| 1020: | 15001015 | c | g |
| 1021: | 15001541 | t | c |
| 1022: | 15003015 | t | c |
| 1023: | 15003295 | c | t |
| 1024: | 15003506 | c | a |
| 1025: | 15003702 | t | g |
| 1026: | 15004887 | a | t |
| 1027: | 15005096 | c | g |
| 1028: | 15005343 | t | c |
| 1029: | 15005979 | g | t |
| 1030: | 15006994 | a | t |
| 1031: | 15012376 | g | c |
| 1032: | 15012478 | c | t |
| 1033: | 15013750 | a | g |
| 1034: | 15013958 | c | t |
| 1035: | 15014963 | g | a |
| 1036: | 15016330 | a | g |
| 1037: | 15017158 | g | a |
| 1038: | 15017812 | t | c |
| 1039: | 15018193 | t | c |
| 1040: | 15018598 | c | t |
| 1041: | 15019575 | t | c |
| 1042: | 15020203 | t | c |
| 1043: | 15020215 | a | g |
| 1044: | 15020761 | c | t |
| 1045: | 15021675 | g | a |
| 1046: | 15024870 | a | c |
| 1047: | 15027668 | a | g |
| 1048: | 15028233 | a | t |
| 1049: | 15030226 | t | c |
| 1050: | 15030777 | c | t |
| 1051: | 15031770 | a | c |
| 1052: | 15031862 | a | g |
| 1053: | 15032108 | t | c |
| 1054: | 15032579 | g | a |
| 1055: | 15042603 | c | g |
| 1056: | 15042663 | g | a |
| 1057: | 15043235 | a | g |
| 1058: | 15044312 | c | t |
| 1059: | 15044487 | g | c |

TABLE 1-continued

| POSITION | REFERENCE_BASE | ALTERNATE_BASE |
|---|---|---|
| 1060: 15044714 | g | a |
| 1061: 15044802 | c | t |
| 1062: 15044846 | g | c |
| 1063: 15045769 | t | c |
| 1064: 15046216 | g | t |
| 1065: 15047935 | t | c |
| 1066: 15048235 | g | a |
| 1067: 15049641 | g | a |
| 1068: 15052050 | a | c |
| 1069: 15052308 | g | c |
| 1070: 15052666 | g | t |
| 1071: 15052897 | t | g |
| 1072: 15053077 | c | t |
| 1073: 15053098 | g | a |
| 1074: 15053372 | g | t |
| 1075: 15053906 | a | g |
| 1076: 15053965 | g | a |
| 1077: 15054237 | t | g |
| 1078: 15054358 | g | t |
| 1079: 15054369 | a | t |
| 1080: 15054413 | a | g |
| 1081: 15054623 | c | t |
| 1082: 15055285 | a | g |
| 1083: 15056247 | t | c |
| 1084: 15056262 | c | a |
| 1085: 15056524 | c | g |
| 1086: 15056732 | t | g |
| 1087: 15057645 | c | t |
| 1088: 15057911 | a | g |
| 1089: 15059081 | t | c |
| 1090: 15059227 | t | c |
| 1091: 15059251 | g | t |
| 1092: 15059355 | t | c |
| 1093: 15059511 | a | g |
| 1094: 15059676 | g | c |
| 1095: 15059704 | g | c |
| 1096: 15061168 | a | c |
| 1097: 15061851 | a | g |
| 1098: 15062050 | a | c |
| 1099: 15062336 | a | c |
| 1100: 15062876 | t | c |
| 1101: 15062902 | c | t |
| 1102: 15063240 | c | t |
| 1103: 15063278 | g | c |
| 1104: 15063388 | t | c |
| 1105: 15063738 | t | c |
| 1106: 15063889 | g | a |
| 1107: 15064072 | t | c |
| 1108: 15064135 | c | t |
| 1109: 15064449 | c | t |
| 1110: 15064468 | t | c |
| 1111: 15064803 | t | g |
| 1112: 15064825 | a | g |
| 1113: 15083316 | g | t |
| 1114: 15083539 | a | c |
| 1115: 15085015 | a | g |
| 1116: 15087382 | c | t |
| 1117: 15087549 | c | t |
| 1118: 15087811 | a | c |
| 1119: 15088024 | g | a |
| 1120: 15088408 | c | t |
| 1121: 15089510 | c | t |
| 1122: 15090351 | a | g |
| 1123: 15091082 | g | a |
| 1124: 15091800 | c | g |
| 1125: 15091818 | g | c |
| 1126: 15091931 | t | c |
| 1127: 15092491 | c | t |
| 1128: 15092600 | c | t |
| 1129: 15093766 | t | g |
| 1130: 15094258 | c | t |
| 1131: 15095449 | t | c |
| 1132: 15096410 | g | c |
| 1133: 15096417 | t | c |
| 1134: 15097205 | t | a |
| 1135: 15099623 | a | g |
| 1136: 15100929 | a | g |
| 1137: 15102290 | a | g |
| 1138: 15102639 | t | c |
| 1139: 15103451 | g | a |
| 1140: 15103501 | t | a |
| 1141: 15103594 | g | c |
| 1142: 15103649 | t | c |
| 1143: 15103944 | g | c |
| 1144: 15104691 | c | t |
| 1145: 15105602 | c | t |
| 1146: 15105975 | t | c |
| 1147: 15108357 | g | a |
| 1148: 15112061 | g | c |
| 1149: 15113179 | g | c |
| 1150: 15113322 | a | t |
| 1151: 15113753 | t | c |
| 1152: 15113838 | c | a |
| 1153: 15113882 | c | t |
| 1154: 15113898 | t | c |
| 1155: 15114339 | c | t |
| 1156: 15114389 | a | g |
| 1157: 15114648 | g | a |
| 1158: 15114880 | a | g |
| 1159: 15114984 | c | t |
| 1160: 15114985 | g | a |
| 1161: 15115208 | g | c |
| 1162: 15115270 | g | t |
| 1163: 15115470 | a | g |
| 1164: 15115656 | g | a |
| 1165: 15115762 | g | c |
| 1166: 15115798 | t | c |
| 1167: 15115868 | a | g |
| 1168: 15115872 | c | g |
| 1169: 15116056 | a | c |
| 1170: 15116070 | t | g |
| 1171: 15116562 | c | t |
| 1172: 15117228 | g | a |
| 1173: 15117343 | g | a |
| 1174: 15117378 | t | c |
| 1175: 15117616 | g | c |
| 1176: 15118147 | t | a |
| 1177: 15118222 | a | g |
| 1178: 15118294 | c | t |
| 1179: 15118320 | c | a |
| 1180: 15118721 | a | c |
| 1181: 15118824 | g | a |
| 1182: 15119382 | g | t |
| 1183: 15120030 | t | a |
| 1184: 15120282 | t | c |
| 1185: 15120655 | c | t |
| 1186: 15120709 | a | c |
| 1187: 15121042 | g | t |
| 1188: 15121068 | a | g |
| 1189: 15121138 | c | t |
| 1190: 15121152 | c | a |
| 1191: 15121365 | t | c |
| 1192: 15121476 | c | t |
| 1193: 15121504 | a | g |
| 1194: 15121563 | g | a |
| 1195: 15121698 | c | t |
| 1196: 15121918 | a | g |
| 1197: 15122456 | c | g |
| 1198: 15122528 | g | c |
| 1199: 15122576 | c | t |
| 1200: 15123075 | c | t |
| 1201: 15123299 | t | c |
| 1202: 15125594 | g | c |
| 1203: 15129221 | a | c |
| 1204: 15129277 | t | c |
| 1205: 15129443 | t | c |
| 1206: 15130654 | t | c |
| 1207: 15130816 | a | g |
| 1208: 15133882 | t | g |
| 1209: 15135489 | a | c |
| 1210: 15137526 | t | c |
| 1211: 15137760 | g | a |
| 1212: 15137880 | t | c |
| 1213: 15137947 | a | g |

TABLE 1-continued

| | POSITION | REFERENCE_BASE | ALTERNATE_BASE |
|---|---|---|---|
| 1214: | 15138114 | t | c |
| 1215: | 15140503 | t | c |
| 1216: | 15140594 | g | a |
| 1217: | 15143181 | t | c |
| 1218: | 15143437 | t | g |
| 1219: | 15143561 | g | a |
| 1220: | 15155635 | g | c |
| 1221: | 15156184 | a | g |
| 1222: | 15156288 | g | c |
| 1223: | 15156843 | g | c |
| 1224: | 15156864 | c | a |
| 1225: | 15157266 | a | g |
| 1226: | 15157366 | a | g |
| 1227: | 15157750 | g | a |
| 1228: | 15157932 | c | t |
| 1229: | 15158367 | t | c |
| 1230: | 15158954 | g | a |
| 1231: | 15159251 | a | g |
| 1232: | 15159681 | t | g |
| 1233: | 15159905 | t | c |
| 1234: | 15160103 | c | g |
| 1235: | 15160229 | g | a |
| 1236: | 15160375 | a | g |
| 1237: | 15160747 | a | g |
| 1238: | 15161208 | a | g |
| 1239: | 15161296 | t | c |
| 1240: | 15162116 | a | g |
| 1241: | 15162818 | c | g |
| 1242: | 15163393 | g | a |
| 1243: | 15163709 | a | g |
| 1244: | 15164061 | g | t |
| 1245: | 15164535 | a | c |
| 1246: | 15164606 | a | g |
| 1247: | 15164956 | a | g |
| 1248: | 15165414 | g | t |
| 1249: | 15165880 | a | g |
| 1250: | 15166496 | a | g |
| 1251: | 15166944 | c | t |
| 1252: | 15170886 | g | t |
| 1253: | 15171082 | a | c |
| 1254: | 15171234 | a | t |
| 1255: | 15171477 | t | c |
| 1256: | 15171575 | g | a |
| 1257: | 15172248 | c | t |
| 1258: | 15172591 | t | c |
| 1259: | 15172663 | c | t |
| 1260: | 15173690 | c | g |
| 1261: | 15173999 | t | c |
| 1262: | 15174464 | c | g |
| 1263: | 15174576 | c | a |
| 1264: | 15174731 | g | t |
| 1265: | 15179847 | c | g |
| 1266: | 15181517 | a | g |
| 1267: | 15182912 | g | a |
| 1268: | 15188258 | c | g |
| 1269: | 15188944 | c | g |
| 1270: | 15190568 | a | g |
| 1271: | 15193056 | c | a |
| 1272: | 15193235 | a | c |
| 1273: | 15196894 | c | g |
| 1274: | 15197392 | c | g |
| 1275: | 15197616 | c | t |
| 1276: | 15198273 | a | g |
| 1277: | 15200470 | a | g |
| 1278: | 15201112 | c | t |
| 1279: | 15201163 | a | g |
| 1280: | 15210195 | a | g |
| 1281: | 15210821 | g | a |
| 1282: | 15210892 | c | t |
| 1283: | 15211414 | t | c |
| 1284: | 15213038 | t | c |
| 1285: | 15213698 | a | g |
| 1286: | 15218585 | c | t |
| 1287: | 15219179 | c | g |
| 1288: | 15219910 | t | g |
| 1289: | 15219979 | t | c |
| 1290: | 15220030 | c | a |
| 1291: | 15221507 | t | c |
| 1292: | 15221812 | a | g |
| 1293: | 15222360 | g | c |
| 1294: | 15235712 | a | c |
| 1295: | 15236093 | g | a |
| 1296: | 15237058 | t | c |
| 1297: | 15237243 | t | a |
| 1298: | 15237826 | g | a |
| 1299: | 15245937 | g | a |
| 1300: | 15247814 | a | c |
| 1301: | 15248287 | a | t |
| 1302: | 15248858 | a | g |
| 1303: | 15249464 | a | c |
| 1304: | 15249918 | g | a |
| 1305: | 15250861 | a | g |
| 1306: | 15257591 | a | g |
| 1307: | 15258299 | c | g |
| 1308: | 15258781 | t | a |
| 1309: | 15259393 | g | c |
| 1310: | 15278236 | a | g |
| 1311: | 15278332 | g | c |
| 1312: | 15278864 | a | g |
| 1313: | 15280727 | c | t |
| 1314: | 15281279 | a | g |
| 1315: | 15284038 | a | g |
| 1316: | 15286073 | t | a |
| 1317: | 15286767 | c | t |
| 1318: | 15287268 | g | a |
| 1319: | 15287757 | t | c |
| 1320: | 15288157 | c | t |
| 1321: | 15290861 | a | g |
| 1322: | 15292602 | t | g |
| 1323: | 15292856 | a | t |
| 1324: | 15292946 | a | t |
| 1325: | 15294452 | t | c |
| 1326: | 15294619 | a | g |
| 1327: | 15295190 | c | t |
| 1328: | 15295340 | c | g |
| 1329: | 15295448 | g | a |
| 1330: | 15295751 | a | g |
| 1331: | 15296044 | t | c |
| 1332: | 15298911 | c | t |
| 1333: | 15299701 | a | g |
| 1334: | 15301236 | t | c |
| 1335: | 15301721 | a | g |
| 1336: | 15302795 | c | t |
| 1337: | 15304359 | c | t |
| 1338: | 15304768 | c | t |
| 1339: | 15305451 | c | t |
| 1340: | 15305499 | c | t |
| 1341: | 15306159 | a | g |
| 1342: | 15307257 | c | t |
| 1343: | 15326402 | c | g |
| 1344: | 15327372 | g | a |
| 1345: | 15327854 | t | c |
| 1346: | 15328122 | c | t |
| 1347: | 15329473 | a | g |
| 1348: | 15330241 | a | g |
| 1349: | 15330332 | c | t |
| 1350: | 15330473 | g | a |
| 1351: | 15330915 | a | c |
| 1352: | 15334013 | t | a |
| 1353: | 15335579 | c | t |
| 1354: | 15335902 | g | c |
| 1355: | 15337003 | t | c |
| 1356: | 15337602 | c | t |
| 1357: | 15337928 | c | t |
| 1358: | 15338527 | g | c |
| 1359: | 15338830 | t | c |
| 1360: | 15339015 | c | t |
| 1361: | 15339975 | g | a |
| 1362: | 15340878 | c | t |
| 1363: | 15340950 | c | t |
| 1364: | 15342242 | t | c |
| 1365: | 15342864 | a | g |
| 1366: | 15343377 | c | a |
| 1367: | 15343820 | a | g |

TABLE 1-continued

| | POSITION | REFERENCE_BASE | ALTERNATE_BASE |
|---|---|---|---|
| 1368: | 15343964 | g | a |
| 1369: | 15344149 | a | g |
| 1370: | 15344260 | a | g |
| 1371: | 15344700 | a | c |
| 1372: | 15345417 | c | t |
| 1373: | 15345590 | c | t |
| 1374: | 15345802 | a | g |
| 1375: | 15345997 | g | t |
| 1376: | 15346966 | c | t |
| 1377: | 15347172 | t | c |
| 1378: | 15347358 | t | g |
| 1379: | 15347471 | c | t |
| 1380: | 15347710 | c | t |
| 1381: | 15347796 | c | a |
| 1382: | 15347920 | a | g |
| 1383: | 15348439 | g | c |
| 1384: | 15348529 | c | t |
| 1385: | 15348906 | t | c |
| 1386: | 15349540 | a | g |
| 1387: | 15350434 | c | t |
| 1388: | 15350912 | g | a |
| 1389: | 15357981 | g | a |
| 1390: | 15358427 | c | t |
| 1391: | 15360697 | a | g |
| 1392: | 15360917 | t | c |
| 1393: | 15360943 | c | t |
| 1394: | 15363937 | a | t |
| 1395: | 15366193 | a | g |
| 1396: | 15366365 | a | c |
| 1397: | 15367309 | t | c |
| 1398: | 15367886 | c | t |
| 1399: | 15368346 | c | a |
| 1400: | 15369041 | a | g |
| 1401: | 15369192 | c | g |
| 1402: | 15371582 | t | c |
| 1403: | 15371834 | g | a |
| 1404: | 15372859 | t | a |
| 1405: | 15372883 | g | c |
| 1406: | 15373382 | c | t |
| 1407: | 15376003 | t | c |
| 1408: | 15376545 | g | c |
| 1409: | 15377765 | g | a |
| 1410: | 15377859 | t | a |
| 1411: | 15378300 | g | t |
| 1412: | 15379758 | g | a |
| 1413: | 15380744 | t | c |
| 1414: | 15381135 | t | g |
| 1415: | 15381405 | t | c |
| 1416: | 15381459 | c | t |
| 1417: | 15381699 | g | c |
| 1418: | 15381786 | c | t |
| 1419: | 15381927 | g | a |
| 1420: | 15383192 | t | c |
| 1421: | 15383785 | t | c |
| 1422: | 15385245 | t | c |
| 1423: | 15385354 | c | a |
| 1424: | 15386150 | c | t |
| 1425: | 15386401 | a | g |
| 1426: | 15387951 | a | t |
| 1427: | 15387995 | c | g |
| 1428: | 15389985 | t | c |
| 1429: | 15390251 | a | g |
| 1430: | 15390643 | g | a |
| 1431: | 15392267 | c | t |
| 1432: | 15409236 | c | t |
| 1433: | 15410370 | g | a |
| 1434: | 15410509 | g | a |
| 1435: | 15411476 | t | c |
| 1436: | 15412787 | t | c |
| 1437: | 15414565 | t | c |
| 1438: | 15414892 | t | a |
| 1439: | 15415790 | t | c |
| 1440: | 15416105 | t | c |
| 1441: | 15416836 | c | g |
| 1442: | 15418302 | t | c |
| 1443: | 15419812 | t | a |
| 1444: | 15423572 | a | t |
| 1445: | 15424068 | a | g |
| 1446: | 15425337 | t | a |
| 1447: | 15425888 | t | g |
| 1448: | 15427076 | c | t |
| 1449: | 15427774 | c | t |
| 1450: | 15428455 | c | a |
| 1451: | 15430737 | c | t |
| 1452: | 15430820 | a | g |
| 1453: | 15430977 | a | g |
| 1454: | 15431009 | a | g |
| 1455: | 15431108 | g | a |
| 1456: | 15431384 | a | g |
| 1457: | 15431734 | t | c |
| 1458: | 15432013 | t | g |
| 1459: | 15432686 | t | g |
| 1460: | 15437902 | c | g |
| 1461: | 15438917 | c | t |
| 1462: | 15439622 | g | a |
| 1463: | 15443427 | a | t |
| 1464: | 15443645 | c | t |
| 1465: | 15443857 | a | g |
| 1466: | 15444727 | t | c |
| 1467: | 15450381 | g | a |
| 1468: | 15450655 | t | c |
| 1469: | 15451393 | a | c |
| 1470: | 15453228 | t | c |
| 1471: | 15454485 | c | t |
| 1472: | 15457603 | t | c |
| 1473: | 15458762 | t | c |
| 1474: | 15460247 | c | t |
| 1475: | 15460565 | g | a |
| 1476: | 15462506 | a | g |
| 1477: | 15463003 | g | a |
| 1478: | 15463092 | a | c |
| 1479: | 15464063 | g | c |
| 1480: | 15464626 | t | c |
| 1481: | 15464934 | t | c |
| 1482: | 15465284 | a | c |
| 1483: | 15467849 | t | c |
| 1484: | 15468390 | t | g |
| 1485: | 15471797 | t | c |
| 1486: | 15472451 | c | t |
| 1487: | 15473157 | g | a |
| 1488: | 15473855 | c | a |
| 1489: | 15474519 | a | g |
| 1490: | 15474878 | a | c |
| 1491: | 15475161 | t | g |
| 1492: | 15475625 | g | a |
| 1493: | 15476413 | t | c |
| 1494: | 15478861 | a | g |
| 1495: | 15479973 | t | c |
| 1496: | 15487398 | t | c |
| 1497: | 15490194 | g | a |
| 1498: | 15490358 | c | a |
| 1499: | 15491723 | c | g |
| 1500: | 15495785 | c | t |
| 1501: | 15496171 | g | a |
| 1502: | 15496250 | a | g |
| 1503: | 15498854 | g | c |
| 1504: | 15499196 | g | c |
| 1505: | 15499256 | a | c |
| 1506: | 15523006 | c | t |
| 1507: | 15523665 | a | g |
| 1508: | 15524016 | t | c |
| 1509: | 15527375 | a | t |
| 1510: | 15527457 | t | a |
| 1511: | 15527780 | a | g |
| 1512: | 15529195 | t | c |
| 1513: | 15529261 | a | g |
| 1514: | 15529955 | t | c |
| 1515: | 15532781 | c | t |
| 1516: | 15533397 | g | a |
| 1517: | 15533879 | t | c |
| 1518: | 15534695 | g | t |
| 1519: | 15535616 | g | a |
| 1520: | 15536274 | a | c |
| 1521: | 15536511 | c | t |

TABLE 1-continued

| POSITION | | REFERENCE_BASE | ALTERNATE_BASE |
|---|---|---|---|
| 1522: | 15536677 | g | a |
| 1523: | 15536799 | c | a |
| 1524: | 15537359 | t | g |
| 1525: | 15537618 | a | c |
| 1526: | 15537702 | g | t |
| 1527: | 15538279 | c | t |
| 1528: | 15538634 | c | t |
| 1529: | 15538756 | c | t |
| 1530: | 15540283 | c | t |
| 1531: | 15540330 | a | t |
| 1532: | 15540502 | a | g |
| 1533: | 15540516 | c | g |
| 1534: | 15540890 | t | c |
| 1535: | 15541750 | t | c |
| 1536: | 15541758 | g | a |
| 1537: | 15542644 | t | c |
| 1538: | 15543464 | a | g |
| 1539: | 15546803 | g | t |
| 1540: | 15551175 | c | t |
| 1541: | 15552203 | t | c |
| 1542: | 15552298 | c | a |
| 1543: | 15552852 | c | g |
| 1544: | 15554945 | c | t |
| 1545: | 15556161 | g | t |
| 1546: | 15556541 | g | a |
| 1547: | 15563972 | c | t |
| 1548: | 15564801 | g | a |
| 1549: | 15566839 | c | t |
| 1550: | 15569911 | a | g |
| 1551: | 15577877 | c | t |
| 1552: | 15578595 | c | t |
| 1553: | 15580026 | c | t |
| 1554: | 15580045 | t | c |
| 1555: | 15580175 | c | t |
| 1556: | 15580249 | a | c |
| 1557: | 15582161 | a | g |
| 1558: | 15582688 | t | c |
| 1559: | 15582848 | c | t |
| 1560: | 15582933 | c | t |
| 1561: | 15586302 | a | g |
| 1562: | 15587858 | c | g |
| 1563: | 15588925 | c | g |
| 1564: | 15591800 | a | t |
| 1565: | 15591859 | c | g |
| 1566: | 15600225 | c | t |
| 1567: | 15608114 | t | c |
| 1568: | 15608937 | g | a |
| 1569: | 15616547 | c | t |
| 1570: | 15616879 | t | c |
| 1571: | 15617219 | t | g |
| 1572: | 15618262 | t | a |
| 1573: | 15618417 | c | g |
| 1574: | 15618515 | c | t |
| 1575: | 15620129 | g | a |
| 1576: | 15621865 | c | t |
| 1577: | 15622109 | c | t |
| 1578: | 15637711 | g | a |
| 1579: | 15638452 | t | c |
| 1580: | 15638866 | a | g |
| 1581: | 15639437 | g | c |
| 1582: | 15642518 | a | g |
| 1583: | 15642674 | g | a |
| 1584: | 15645314 | c | t |
| 1585: | 15648663 | c | t |
| 1586: | 15649103 | a | c |
| 1587: | 15654686 | a | c |
| 1588: | 15656541 | t | c |
| 1589: | 15657411 | g | a |
| 1590: | 15658739 | c | t |
| 1591: | 15663546 | c | g |
| 1592: | 15663679 | a | g |
| 1593: | 15663852 | g | t |
| 1594: | 15663985 | g | t |
| 1595: | 15664082 | g | c |
| 1596: | 15664145 | g | a |
| 1597: | 15669261 | g | a |
| 1598: | 15670027 | t | c |

TABLE 1-continued

| POSITION | | REFERENCE_BASE | ALTERNATE_BASE |
|---|---|---|---|
| 1599: | 15670322 | t | c |
| 1600: | 15671011 | g | c |
| 1601: | 15673660 | g | a |
| 1602: | 15674299 | c | t |
| 1603: | 15676072 | g | a |
| 1604: | 15676310 | t | g |
| 1605: | 15676356 | a | g |
| 1606: | 15676616 | c | g |
| 1607: | 15676688 | t | c |
| 1608: | 15677147 | c | t |
| 1609: | 15679492 | c | t |
| 1610: | 15679661 | g | a |
| 1611: | 15681218 | g | c |
| 1612: | 15681673 | a | g |
| 1613: | 15682323 | a | g |
| 1614: | 15682327 | t | a |
| 1615: | 15682496 | t | g |
| 1616: | 15682558 | c | t |
| 1617: | 15682686 | a | g |
| 1618: | 15682767 | t | c |
| 1619: | 15683565 | t | c |
| 1620: | 15684832 | g | a |
| 1621: | 15687108 | c | g |
| 1622: | 15687904 | t | c |
| 1623: | 15688284 | t | c |
| 1624: | 15688553 | c | t |
| 1625: | 15689098 | g | t |
| 1626: | 15689545 | t | c |
| 1627: | 15690113 | a | g |
| 1628: | 15690137 | g | a |
| 1629: | 15690191 | t | c |
| 1630: | 15690624 | g | a |
| 1631: | 15690902 | a | g |
| 1632: | 15691598 | c | a |
| 1633: | 15692228 | c | g |
| 1634: | 15692260 | c | t |
| 1635: | 15692271 | c | t |
| 1636: | 15692337 | t | c |
| 1637: | 15692526 | c | t |
| 1638: | 15692586 | t | c |
| 1639: | 15692696 | g | a |
| 1640: | 15692747 | c | t |
| 1641: | 15692833 | t | c |
| 1642: | 15693076 | t | g |
| 1643: | 15693152 | a | c |
| 1644: | 15693231 | g | a |
| 1645: | 15693325 | c | t |
| 1646: | 15693734 | a | g |
| 1647: | 15693746 | c | t |
| 1648: | 15694033 | t | g |
| 1649: | 15694052 | t | c |
| 1650: | 15694619 | a | g |
| 1651: | 15694659 | t | c |
| 1652: | 15703901 | g | c |
| 1653: | 15707451 | a | c |
| 1654: | 15707939 | g | c |
| 1655: | 15707979 | g | c |
| 1656: | 15708291 | g | a |
| 1657: | 15708450 | g | a |
| 1658: | 15709137 | c | t |
| 1659: | 15710288 | g | c |
| 1660: | 15710413 | t | g |
| 1661: | 15711217 | t | c |
| 1662: | 15712103 | c | t |
| 1663: | 15712240 | t | c |
| 1664: | 15713181 | c | t |
| 1665: | 15713268 | c | t |
| 1666: | 15714196 | g | t |
| 1667: | 15714283 | c | t |
| 1668: | 15714821 | t | c |
| 1669: | 15714913 | t | c |
| 1670: | 15715978 | a | c |
| 1671: | 15718084 | a | g |
| 1672: | 15718481 | c | t |
| 1673: | 15718631 | a | c |
| 1674: | 15718740 | a | c |
| 1675: | 15718816 | g | a |

TABLE 1-continued

| POSITION | REFERENCE_BASE | ALTERNATE_BASE |
|---|---|---|
| 1676: 15722417 | c | a |
| 1677: 15724448 | c | g |
| 1678: 15730898 | c | a |
| 1679: 15731033 | c | g |
| 1680: 15732704 | a | g |
| 1681: 15733164 | g | t |
| 1682: 15733187 | c | t |
| 1683: 15736091 | t | c |
| 1684: 15736526 | g | a |
| 1685: 15737076 | a | g |
| 1686: 15739695 | a | c |
| 1687: 15739891 | g | a |
| 1688: 15740481 | c | a |
| 1689: 15751366 | a | g |
| 1690: 15753534 | t | g |
| 1691: 15756338 | c | t |
| 1692: 15759372 | a | g |
| 1693: 15762194 | c | t |
| 1694: 15773733 | a | g |
| 1695: 15777456 | g | c |
| 1696: 15778730 | c | t |
| 1697: 15779025 | g | a |
| 1698: 15783049 | a | g |
| 1699: 15783412 | c | t |
| 1700: 15799315 | g | a |
| 1701: 15799533 | t | c |
| 1702: 15806274 | c | a |
| 1703: 15809218 | t | c |
| 1704: 15816136 | c | t |
| 1705: 15817833 | c | t |
| 1706: 15818484 | c | t |
| 1707: 15819000 | c | t |
| 1708: 15819001 | g | a |
| 1709: 15819890 | a | t |
| 1710: 15820114 | a | g |
| 1711: 15828926 | g | a |
| 1712: 15829019 | g | c |
| 1713: 15829255 | g | t |
| 1714: 15830468 | a | g |
| 1715: 15831550 | g | t |
| 1716: 15832981 | c | t |
| 1717: 15834204 | a | g |
| 1718: 15835339 | a | g |
| 1719: 15836962 | c | t |
| 1720: 15842893 | c | t |
| 1721: 15843308 | a | g |
| 1722: 15845674 | a | g |
| 1723: 15847522 | a | g |
| 1724: 15848497 | a | g |
| 1725: 15848531 | a | g |
| 1726: 15849033 | g | a |
| 1727: 15849827 | a | g |
| 1728: 15850206 | c | t |
| 1729: 15850845 | a | t |
| 1730: 15851620 | c | a |
| 1731: 15852141 | c | t |
| 1732: 15853572 | c | t |
| 1733: 15853834 | c | t |
| 1734: 15854287 | c | t |
| 1735: 15854345 | g | t |
| 1736: 15854383 | c | t |
| 1737: 15854491 | t | c |
| 1738: 15854988 | a | g |
| 1739: 15855036 | g | a |
| 1740: 15856634 | t | c |
| 1741: 15857906 | a | g |
| 1742: 15858997 | t | c |
| 1743: 15874301 | g | a |
| 1744: 15875743 | a | g |
| 1745: 15887486 | t | c |
| 1746: 15889701 | a | g |
| 1747: 15890290 | t | g |
| 1748: 15890995 | g | t |
| 1749: 15892019 | g | t |
| 1750: 15896400 | t | g |
| 1751: 15897571 | a | t |
| 1752: 15899275 | t | g |
| 1753: 15902578 | t | g |
| 1754: 15902689 | g | a |
| 1755: 15903864 | t | g |
| 1756: 15919825 | a | g |
| 1757: 15931959 | a | g |
| 1758: 15932046 | c | t |
| 1759: 15932544 | t | c |
| 1760: 15933606 | c | t |
| 1761: 15935097 | g | t |
| 1762: 15935241 | c | t |
| 1763: 15935902 | c | t |
| 1764: 15936345 | a | g |
| 1765: 15937676 | a | t |
| 1766: 15937927 | g | t |
| 1767: 15942035 | c | g |
| 1768: 15943256 | a | g |
| 1769: 15943625 | c | a |
| 1770: 15944014 | t | c |
| 1771: 15983697 | g | t |
| 1772: 15983783 | c | t |
| 1773: 15984281 | a | g |
| 1774: 15986236 | t | a |
| 1775: 15986991 | c | a |
| 1776: 15988284 | a | c |
| 1777: 15992536 | g | a |
| 1778: 16008242 | a | g |
| 1779: 16008657 | t | g |
| 1780: 16009127 | t | c |
| 1781: 16024511 | g | c |
| 1782: 16030603 | t | c |
| 1783: 16030715 | t | c |
| 1784: 16030968 | a | g |
| 1785: 16037236 | c | t |
| 1786: 16038317 | g | a |
| 1787: 16038409 | c | t |
| 1788: 16038497 | c | t |
| 1789: 16038572 | g | c |
| 1790: 16039175 | g | a |
| 1791: 16040204 | g | a |
| 1792: 16041425 | c | t |
| 1793: 16042095 | c | t |
| 1794: 16045383 | c | t |
| 1795: 16045823 | c | t |
| 1796: 16046596 | c | t |
| 1797: 16047021 | a | g |
| 1798: 16047262 | g | t |
| 1799: 16052110 | t | c |
| 1800: 16054857 | g | a |
| 1801: 16056362 | t | g |
| 1802: 16057875 | g | t |
| 1803: 16058116 | g | a |
| 1804: 16058654 | g | a |
| 1805: 16060655 | t | g |
| 1806: 16061286 | a | t |
| 1807: 16062047 | t | c |
| 1808: 16065804 | a | c |
| 1809: 16067677 | g | t |
| 1810: 16070093 | t | c |
| 1811: 16070754 | t | c |
| 1812: 16073742 | g | a |
| 1813: 16075005 | g | a |
| 1814: 16075669 | g | a |
| 1815: 16076345 | a | g |
| 1816: 16077846 | g | a |
| 1817: 16079168 | c | t |
| 1818: 16080584 | a | c |
| 1819: 16081158 | t | c |
| 1820: 16081844 | g | a |
| 1821: 16082851 | a | g |
| 1822: 16085227 | t | g |
| 1823: 16087921 | g | a |
| 1824: 16089418 | a | g |
| 1825: 16098425 | a | g |
| 1826: 16099068 | c | t |
| 1827: 16101029 | c | t |
| 1828: 16101238 | g | a |
| 1829: 16101503 | t | g |

TABLE 1-continued

| POSITION | REFERENCE_BASE | ALTERNATE_BASE |
|---|---|---|
| 1830: 16101922 | t | g |
| 1831: 16102747 | c | t |
| 1832: 16103415 | a | g |
| 1833: 16104748 | a | t |
| 1834: 16105384 | a | g |
| 1835: 16105646 | g | t |
| 1836: 16105738 | a | g |
| 1837: 16106737 | a | c |
| 1838: 16107103 | c | t |
| 1839: 16107196 | g | t |
| 1840: 16108455 | g | t |
| 1841: 16109490 | a | g |
| 1842: 16109580 | a | g |
| 1843: 16110463 | t | a |
| 1844: 16110632 | c | t |
| 1845: 16111189 | g | a |
| 1846: 16111591 | a | g |
| 1847: 16113216 | g | t |
| 1848: 16113257 | g | t |
| 1849: 16113390 | a | t |
| 1850: 16113450 | t | c |
| 1851: 16113549 | c | t |
| 1852: 16116286 | a | t |
| 1853: 16117063 | a | g |
| 1854: 16118964 | c | t |
| 1855: 16120186 | a | g |
| 1856: 16122504 | a | g |
| 1857: 16123008 | a | g |
| 1858: 16123345 | c | t |
| 1859: 16123364 | g | t |
| 1860: 16124187 | g | c |
| 1861: 16125749 | g | t |
| 1862: 16125865 | g | t |
| 1863: 16126708 | t | g |
| 1864: 16126807 | c | g |
| 1865: 16128540 | a | g |
| 1866: 16128689 | g | t |
| 1867: 16130538 | t | c |
| 1868: 16132743 | a | g |
| 1869: 16133485 | c | t |
| 1870: 16136056 | g | c |
| 1871: 16156909 | g | a |
| 1872: 16159187 | c | t |
| 1873: 16159236 | a | g |
| 1874: 16161448 | c | t |
| 1875: 16162085 | a | g |
| 1876: 16163596 | g | a |
| 1877: 16164420 | g | a |
| 1878: 16165307 | a | g |
| 1879: 16166790 | a | g |
| 1880: 16168106 | c | t |
| 1881: 16170838 | t | c |
| 1882: 16172349 | t | g |
| 1883: 16174395 | c | a |
| 1884: 16176693 | a | t |
| 1885: 16177280 | g | a |
| 1886: 16179498 | a | t |
| 1887: 16185288 | c | t |
| 1888: 16189970 | c | a |
| 1889: 16190273 | a | g |
| 1890: 16191151 | a | g |
| 1891: 16192017 | a | g |
| 1892: 16194730 | a | c |
| 1893: 16196493 | a | g |
| 1894: 16236531 | c | t |
| 1895: 16252821 | a | g |
| 1896: 16258852 | c | t |
| 1897: 16259538 | a | c |
| 1898: 16260888 | c | t |
| 1899: 16262068 | c | t |
| 1900: 16262116 | a | g |
| 1901: 16263909 | g | t |
| 1902: 16265700 | g | t |
| 1903: 16271911 | a | g |
| 1904: 16291109 | a | g |
| 1905: 16291287 | c | t |
| 1906: 16291786 | c | t |
| 1907: 16293662 | c | t |
| 1908: 16294248 | c | t |
| 1909: 16294712 | a | g |
| 1910: 16297048 | a | g |
| 1911: 16297346 | c | t |
| 1912: 16297483 | c | t |
| 1913: 16298444 | t | c |
| 1914: 16298955 | a | g |
| 1915: 16299046 | a | g |
| 1916: 16299075 | t | c |
| 1917: 16303288 | a | g |
| 1918: 16315275 | c | a |
| 1919: 16315387 | c | g |
| 1920: 16316186 | a | c |
| 1921: 16316358 | c | t |
| 1922: 16319511 | a | c |
| 1923: 16320378 | c | g |
| 1924: 16322237 | c | t |
| 1925: 16325752 | g | c |
| 1926: 16325830 | a | g |
| 1927: 16326227 | g | a |
| 1928: 16326308 | t | g |
| 1929: 16329069 | a | g |
| 1930: 16329479 | g | a |
| 1931: 16330121 | a | g |
| 1932: 16333100 | c | t |
| 1933: 16378917 | t | g |
| 1934: 16380869 | g | a |
| 1935: 16380899 | t | c |
| 1936: 16381622 | t | g |
| 1937: 16383528 | g | t |
| 1938: 16383899 | g | a |
| 1939: 16384514 | g | a |
| 1940: 16384739 | c | t |
| 1941: 16388633 | c | t |
| 1942: 16392905 | c | t |
| 1943: 16395041 | t | g |
| 1944: 16402116 | g | a |
| 1945: 16406304 | a | t |
| 1946: 16408589 | c | t |
| 1947: 16408986 | t | c |
| 1948: 16424883 | t | c |
| 1949: 16424907 | t | g |
| 1950: 16426165 | t | c |
| 1951: 16428818 | g | a |
| 1952: 16428839 | g | a |
| 1953: 16428970 | a | c |
| 1954: 16428972 | g | a |
| 1955: 16429658 | g | a |
| 1956: 16429834 | c | t |
| 1957: 16431077 | c | t |
| 1958: 16431543 | c | t |
| 1959: 16432062 | c | t |
| 1960: 16432429 | g | a |
| 1961: 16432435 | c | t |
| 1962: 16433600 | t | g |
| 1963: 16434815 | a | t |
| 1964: 16436168 | g | a |
| 1965: 16437161 | c | t |
| 1966: 16439207 | a | g |
| 1967: 16439610 | g | a |
| 1968: 16440409 | a | g |
| 1969: 16440441 | c | t |
| 1970: 16441797 | a | g |
| 1971: 16443967 | t | c |
| 1972: 16444793 | a | t |
| 1973: 16444853 | g | c |
| 1974: 16445966 | c | t |
| 1975: 16447816 | t | c |
| 1976: 16447871 | a | g |
| 1977: 16450392 | c | t |
| 1978: 16450484 | c | t |
| 1979: 16451628 | c | t |
| 1980: 16452996 | t | a |
| 1981: 16453065 | g | a |
| 1982: 16453099 | t | a |
| 1983: 16453301 | c | t |

TABLE 1-continued

| | POSITION | REFERENCE_BASE | ALTERNATE_BASE |
|---|---|---|---|
| 1984: | 16453626 | t | c |
| 1985: | 16453892 | g | c |
| 1986: | 16454879 | t | g |
| 1987: | 16454970 | c | t |
| 1988: | 16454998 | g | t |
| 1989: | 16455090 | g | a |
| 1990: | 16455267 | g | a |
| 1991: | 16455483 | g | a |
| 1992: | 16455652 | g | a |
| 1993: | 16455680 | t | c |
| 1994: | 16456271 | a | g |
| 1995: | 16457699 | g | a |
| 1996: | 16459650 | a | g |
| 1997: | 16463006 | g | a |
| 1998: | 16466533 | a | g |
| 1999: | 16467409 | a | g |
| 2000: | 16488835 | c | t |
| 2001: | 16489507 | t | a |
| 2002: | 16492477 | a | g |
| 2003: | 16492789 | c | t |
| 2004: | 16492991 | a | c |
| 2005: | 16493645 | c | t |
| 2006: | 16497156 | t | a |
| 2007: | 16497493 | a | g |
| 2008: | 16500320 | t | c |
| 2009: | 16501953 | c | t |
| 2010: | 16502443 | a | g |
| 2011: | 16504287 | c | a |
| 2012: | 16505490 | t | c |
| 2013: | 16507808 | t | c |
| 2014: | 16515047 | t | c |
| 2015: | 16516564 | c | t |
| 2016: | 16520502 | a | g |
| 2017: | 16523962 | a | g |
| 2018: | 16533898 | c | t |
| 2019: | 16534022 | c | a |
| 2020: | 16534686 | c | t |
| 2021: | 16535187 | t | g |
| 2022: | 16535264 | a | c |
| 2023: | 16540105 | g | t |
| 2024: | 16541642 | c | t |
| 2025: | 16543307 | t | c |
| 2026: | 16543528 | c | t |
| 2027: | 16543678 | t | c |
| 2028: | 16544628 | g | a |
| 2029: | 16546416 | t | c |
| 2030: | 16547698 | g | a |
| 2031: | 16549783 | t | g |
| 2032: | 16550894 | a | g |
| 2033: | 16551756 | g | t |
| 2034: | 16551848 | g | a |
| 2035: | 16552169 | g | a |
| 2036: | 16556121 | g | a |
| 2037: | 16556709 | g | a |
| 2038: | 16556948 | c | t |
| 2039: | 16557761 | a | g |
| 2040: | 16560196 | a | c |
| 2041: | 16560281 | g | c |
| 2042: | 16561763 | g | a |
| 2043: | 16562461 | a | g |
| 2044: | 16562979 | c | a |
| 2045: | 16563859 | c | a |
| 2046: | 16564752 | a | g |
| 2047: | 16565531 | c | t |
| 2048: | 16566784 | t | c |
| 2049: | 16569372 | c | g |
| 2050: | 16569813 | g | t |
| 2051: | 16570637 | a | g |
| 2052: | 16572679 | t | a |
| 2053: | 16573949 | t | c |
| 2054: | 16576931 | g | a |
| 2055: | 16581310 | c | g |
| 2056: | 16583863 | c | t |
| 2057: | 16585147 | g | a |
| 2058: | 16587573 | g | a |
| 2059: | 16587702 | c | t |
| 2060: | 16587910 | g | a |
| 2061: | 16588289 | g | a |
| 2062: | 16588769 | t | a |
| 2063: | 16588795 | c | g |
| 2064: | 16590838 | c | g |
| 2065: | 16590876 | a | g |
| 2066: | 16591006 | a | c |
| 2067: | 16591349 | a | c |
| 2068: | 16593483 | t | c |
| 2069: | 16593857 | c | t |
| 2070: | 16596827 | c | t |
| 2071: | 16598571 | t | g |
| 2072: | 16598739 | c | t |
| 2073: | 16599040 | a | g |
| 2074: | 16599215 | c | t |
| 2075: | 16599743 | g | a |
| 2076: | 16602713 | t | c |
| 2077: | 16604389 | c | t |
| 2078: | 16609220 | c | t |
| 2079: | 16611949 | g | t |
| 2080: | 16617559 | g | a |
| 2081: | 16618136 | a | g |
| 2082: | 16619778 | c | t |
| 2083: | 16619902 | a | g |
| 2084: | 16620350 | t | c |
| 2085: | 16622028 | t | c |
| 2086: | 16623725 | g | c |
| 2087: | 16626202 | t | c |
| 2088: | 16627334 | g | a |
| 2089: | 16638587 | t | g |
| 2090: | 16639018 | g | a |
| 2091: | 16644919 | c | t |
| 2092: | 16649952 | g | t |
| 2093: | 16650556 | a | c |
| 2094: | 16654586 | t | c |
| 2095: | 16655521 | a | c |
| 2096: | 16657891 | t | c |
| 2097: | 16662394 | c | t |
| 2098: | 16663696 | t | c |
| 2099: | 16672093 | a | g |
| 2100: | 16673519 | a | g |
| 2101: | 16676231 | a | t |
| 2102: | 16677194 | a | g |
| 2103: | 16678005 | c | t |
| 2104: | 16681891 | c | t |
| 2105: | 16682448 | g | a |
| 2106: | 16682764 | g | t |
| 2107: | 16683603 | c | t |
| 2108: | 16684337 | c | t |
| 2109: | 16687109 | c | t |
| 2110: | 16687553 | c | t |
| 2111: | 16698149 | a | g |
| 2112: | 16703153 | c | t |
| 2113: | 16704088 | g | t |
| 2114: | 16704721 | g | a |
| 2115: | 16706524 | c | t |
| 2116: | 16712857 | c | a |
| 2117: | 16713703 | c | t |
| 2118: | 16714465 | t | c |
| 2119: | 16717283 | c | t |
| 2120: | 16719083 | c | g |
| 2121: | 16720040 | a | c |
| 2122: | 16722064 | c | t |
| 2123: | 16722665 | c | t |
| 2124: | 16722699 | a | c |
| 2125: | 16723138 | a | g |
| 2126: | 16724498 | c | t |
| 2127: | 16725584 | c | t |
| 2128: | 16727691 | c | t |
| 2129: | 16728578 | c | g |
| 2130: | 16730217 | g | a |
| 2131: | 16731800 | a | g |
| 2132: | 16733911 | c | t |
| 2133: | 16735683 | a | g |
| 2134: | 16743342 | a | g |
| 2135: | 16743442 | a | t |
| 2136: | 16744767 | a | g |
| 2137: | 16744791 | g | t |

TABLE 1-continued

| | POSITION | REFERENCE_BASE | ALTERNATE_BASE |
|---|---|---|---|
| 2138: | 16748857 | c | t |
| 2139: | 16748996 | a | c |
| 2140: | 16752119 | a | g |
| 2141: | 16752470 | c | t |
| 2142: | 16753545 | a | t |
| 2143: | 16754053 | a | g |
| 2144: | 16754251 | g | a |
| 2145: | 16754776 | g | t |
| 2146: | 16755168 | g | a |
| 2147: | 16757712 | a | g |
| 2148: | 16759565 | a | t |
| 2149: | 16760415 | t | c |
| 2150: | 16761370 | a | g |
| 2151: | 16761835 | a | g |
| 2152: | 16762035 | g | a |
| 2153: | 16762736 | a | t |
| 2154: | 16763708 | a | g |
| 2155: | 16766281 | g | t |
| 2156: | 16768206 | a | g |
| 2157: | 16771694 | t | c |
| 2158: | 16774507 | t | g |
| 2159: | 16774733 | a | g |
| 2160: | 16775835 | g | t |
| 2161: | 16776519 | a | g |
| 2162: | 16777831 | c | t |
| 2163: | 16779515 | a | c |
| 2164: | 16782722 | a | g |
| 2165: | 16783086 | c | g |
| 2166: | 16784610 | a | g |
| 2167: | 16784755 | c | t |
| 2168: | 16785179 | a | t |
| 2169: | 16785666 | a | g |
| 2170: | 16785999 | t | g |
| 2171: | 16787543 | c | t |
| 2172: | 16795739 | t | c |
| 2173: | 16796566 | a | g |
| 2174: | 16796856 | t | g |
| 2175: | 16796880 | c | t |
| 2176: | 16796999 | c | t |
| 2177: | 16799720 | t | a |
| 2178: | 16799744 | g | t |
| 2179: | 16800616 | a | g |
| 2180: | 16800820 | a | g |
| 2181: | 16801701 | a | g |
| 2182: | 16802009 | c | t |
| 2183: | 16802494 | g | t |
| 2184: | 16803878 | c | g |
| 2185: | 16806306 | a | g |
| 2186: | 16806336 | c | t |
| 2187: | 16807209 | c | g |
| 2188: | 16808583 | a | g |
| 2189: | 16808652 | c | t |
| 2190: | 16808814 | c | t |
| 2191: | 16809029 | c | t |
| 2192: | 16812553 | a | g |
| 2193: | 16812701 | a | g |
| 2194: | 16813639 | c | t |
| 2195: | 16815483 | c | t |
| 2196: | 16815577 | c | t |
| 2197: | 16815841 | a | g |
| 2198: | 16815843 | g | c |
| 2199: | 16816019 | a | g |
| 2200: | 16816059 | a | g |
| 2201: | 16816317 | a | g |
| 2202: | 16817225 | a | t |
| 2203: | 16818555 | a | t |
| 2204: | 16818818 | g | t |
| 2205: | 16818964 | c | t |
| 2206: | 16819095 | c | t |
| 2207: | 16819249 | c | t |
| 2208: | 16819284 | t | c |
| 2209: | 16819648 | g | a |
| 2210: | 16819804 | c | t |
| 2211: | 16820603 | t | a |
| 2212: | 16821836 | g | a |
| 2213: | 16822156 | t | c |
| 2214: | 16822435 | c | t |
| 2215: | 16823536 | a | g |
| 2216: | 16824558 | c | t |
| 2217: | 16825720 | a | g |
| 2218: | 16825818 | a | c |
| 2219: | 16827204 | c | t |
| 2220: | 16830108 | c | t |
| 2221: | 16830397 | c | g |
| 2222: | 16830498 | c | t |
| 2223: | 16831213 | g | a |
| 2224: | 16831558 | c | t |
| 2225: | 16831952 | c | t |
| 2226: | 16833630 | c | t |
| 2227: | 16834666 | g | t |
| 2228: | 16837744 | a | g |
| 2229: | 16840235 | g | t |
| 2230: | 16841811 | a | t |
| 2231: | 16843667 | a | c |
| 2232: | 16844435 | a | g |
| 2233: | 16844674 | c | t |
| 2234: | 16845197 | a | t |
| 2235: | 16845649 | a | t |
| 2236: | 16846214 | c | t |
| 2237: | 16846386 | a | c |
| 2238: | 16846454 | g | t |
| 2239: | 16848146 | c | t |
| 2240: | 16848176 | a | t |
| 2241: | 16848187 | g | t |
| 2242: | 16853570 | c | g |
| 2243: | 16853930 | a | t |
| 2244: | 16855524 | c | t |
| 2245: | 16856783 | c | t |
| 2246: | 16856943 | g | t |
| 2247: | 16857246 | a | g |
| 2248: | 16858128 | c | g |
| 2249: | 16858363 | g | t |
| 2250: | 16858651 | a | g |
| 2251: | 16859879 | c | t |
| 2252: | 16863672 | c | t |
| 2253: | 16863916 | c | t |
| 2254: | 16863948 | a | c |
| 2255: | 16864762 | c | t |
| 2256: | 16864828 | c | t |
| 2257: | 16864853 | c | g |
| 2258: | 16865265 | a | g |
| 2259: | 16865281 | c | t |
| 2260: | 16866105 | a | g |
| 2261: | 16866596 | a | g |
| 2262: | 16867521 | c | t |
| 2263: | 16868004 | c | t |
| 2264: | 16869601 | c | t |
| 2265: | 16870540 | a | g |
| 2266: | 16870977 | a | g |
| 2267: | 16871637 | c | t |
| 2268: | 16871682 | c | t |
| 2269: | 16872352 | c | g |
| 2270: | 16872445 | a | g |
| 2271: | 16872513 | c | t |
| 2272: | 16873536 | c | t |
| 2273: | 16873551 | c | t |
| 2274: | 16874074 | g | a |
| 2275: | 16874427 | g | a |
| 2276: | 16874672 | c | t |
| 2277: | 16874682 | t | c |
| 2278: | 16875869 | c | t |
| 2279: | 16876135 | g | a |
| 2280: | 16878301 | a | g |
| 2281: | 16879137 | g | a |
| 2282: | 16879348 | a | c |
| 2283: | 16879891 | a | g |
| 2284: | 16880834 | t | c |
| 2285: | 16881362 | g | a |
| 2286: | 16883482 | c | t |
| 2287: | 16883723 | c | t |
| 2288: | 16883734 | t | c |
| 2289: | 16884089 | c | g |
| 2290: | 16885092 | t | c |
| 2291: | 16886417 | t | c |

TABLE 1-continued

| | POSITION | REFERENCE_BASE | ALTERNATE_BASE |
|---|---|---|---|
| 2292: | 16886727 | g | a |
| 2293: | 16887424 | a | t |
| 2294: | 16890604 | a | g |
| 2295: | 16896664 | c | t |
| 2296: | 16898101 | c | t |
| 2297: | 16898260 | t | a |
| 2298: | 16899578 | c | t |
| 2299: | 16900098 | g | t |
| 2300: | 16900846 | g | a |
| 2301: | 16901914 | c | t |
| 2302: | 16902527 | c | t |
| 2303: | 16904465 | a | c |
| 2304: | 16904698 | t | c |
| 2305: | 16904975 | t | c |
| 2306: | 16905335 | c | t |
| 2307: | 16908351 | c | t |
| 2308: | 16912877 | a | g |
| 2309: | 16916913 | a | g |
| 2310: | 16917071 | g | t |
| 2311: | 16917391 | c | t |
| 2312: | 16920324 | c | t |
| 2313: | 16922169 | c | t |
| 2314: | 16924197 | a | g |
| 2315: | 16927334 | c | t |
| 2316: | 16927612 | c | t |
| 2317: | 16927788 | g | t |
| 2318: | 16928102 | a | c |
| 2319: | 16928884 | c | t |
| 2320: | 16928891 | a | g |
| 2321: | 16930713 | c | t |
| 2322: | 16942295 | c | t |
| 2323: | 16942792 | t | c |
| 2324: | 16943247 | a | c |
| 2325: | 16943397 | c | a |
| 2326: | 16943665 | g | c |
| 2327: | 16944587 | g | a |
| 2328: | 16947283 | t | c |
| 2329: | 16947772 | a | g |
| 2330: | 16949409 | c | t |
| 2331: | 16950477 | a | g |
| 2332: | 16950490 | g | a |
| 2333: | 16951179 | c | t |
| 2334: | 16955606 | g | a |
| 2335: | 16956227 | c | t |
| 2336: | 16958742 | c | t |
| 2337: | 16960971 | a | g |
| 2338: | 16961217 | t | c |
| 2339: | 16962181 | g | a |
| 2340: | 16971945 | c | t |
| 2341: | 16973113 | g | a |
| 2342: | 16976508 | c | t |
| 2343: | 16976818 | c | t |
| 2344: | 16977331 | g | t |
| 2345: | 16977735 | g | t |
| 2346: | 16978248 | c | t |
| 2347: | 16979367 | c | t |
| 2348: | 16979874 | a | g |
| 2349: | 16993160 | g | a |
| 2350: | 16995627 | c | t |
| 2351: | 17004286 | t | c |
| 2352: | 17005471 | a | g |
| 2353: | 17008762 | t | a |
| 2354: | 17008813 | g | c |
| 2355: | 17009247 | g | a |
| 2356: | 17011384 | t | c |
| 2357: | 17013671 | a | g |
| 2358: | 17016246 | t | c |
| 2359: | 17016775 | g | c |
| 2360: | 17016968 | a | t |
| 2361: | 17019839 | g | a |
| 2362: | 17020081 | t | c |
| 2363: | 17020531 | g | a |
| 2364: | 17021389 | c | t |
| 2365: | 17022221 | c | a |
| 2366: | 17029189 | a | g |
| 2367: | 17029262 | t | c |
| 2368: | 17029400 | t | c |
| 2369: | 17030590 | c | t |
| 2370: | 17032625 | g | c |
| 2371: | 17033421 | a | t |
| 2372: | 17034591 | a | g |
| 2373: | 17034702 | g | a |
| 2374: | 17035655 | c | t |
| 2375: | 17035787 | g | c |
| 2376: | 17037151 | c | t |
| 2377: | 17037292 | g | a |
| 2378: | 17037591 | a | g |
| 2379: | 17038295 | t | a |
| 2380: | 17038536 | t | c |
| 2381: | 17039288 | g | c |
| 2382: | 17039463 | g | a |
| 2383: | 17040033 | c | t |
| 2384: | 17040685 | c | t |
| 2385: | 17041074 | a | g |
| 2386: | 17041228 | a | g |
| 2387: | 17041460 | g | a |
| 2388: | 17043023 | a | g |
| 2389: | 17043048 | t | c |
| 2390: | 17043184 | g | t |
| 2391: | 17043204 | c | t |
| 2392: | 17043403 | g | a |
| 2393: | 17043435 | a | c |
| 2394: | 17043582 | a | g |
| 2395: | 17043628 | c | t |
| 2396: | 17043701 | c | a |
| 2397: | 17043859 | c | t |
| 2398: | 17043917 | t | c |
| 2399: | 17044276 | t | g |
| 2400: | 17044381 | c | t |
| 2401: | 17048026 | a | c |
| 2402: | 17048802 | a | g |
| 2403: | 17048819 | c | t |
| 2404: | 17050065 | a | c |
| 2405: | 17050498 | c | t |
| 2406: | 17050752 | a | g |
| 2407: | 17051948 | t | c |
| 2408: | 17052061 | g | a |
| 2409: | 17052323 | t | a |
| 2410: | 17052917 | c | g |
| 2411: | 17053470 | c | t |
| 2412: | 17053715 | c | a |
| 2413: | 17054185 | t | g |
| 2414: | 17056558 | g | a |
| 2415: | 17056586 | g | t |
| 2416: | 17056876 | g | a |
| 2417: | 17058951 | g | c |
| 2418: | 17059275 | t | c |
| 2419: | 17064318 | t | c |
| 2420: | 17074891 | c | g |
| 2421: | 17075475 | c | t |
| 2422: | 17084995 | c | g |
| 2423: | 17097466 | a | g |
| 2424: | 17100532 | t | c |
| 2425: | 17101415 | t | c |
| 2426: | 17104923 | c | t |
| 2427: | 17116490 | g | t |
| 2428: | 17117129 | c | a |
| 2429: | 17124515 | c | a |
| 2430: | 17124695 | a | g |
| 2431: | 17129720 | g | a |
| 2432: | 17130119 | g | a |
| 2433: | 17130206 | a | g |
| 2434: | 17130661 | t | c |
| 2435: | 17131330 | a | g |
| 2436: | 17133673 | a | g |
| 2437: | 17134655 | c | t |
| 2438: | 17135022 | g | a |
| 2439: | 17137090 | g | a |
| 2440: | 17139973 | c | g |
| 2441: | 17140500 | t | a |
| 2442: | 17143932 | t | c |
| 2443: | 17144116 | a | t |
| 2444: | 17145410 | g | a |
| 2445: | 17145466 | t | c |

TABLE 1-continued

| POSITION | REFERENCE_BASE | ALTERNATE_BASE |
|---|---|---|
| 2446: 17166120 | a | g |
| 2447: 17170000 | a | g |
| 2448: 17176457 | t | c |
| 2449: 17176592 | c | t |
| 2450: 17179359 | g | a |
| 2451: 17182743 | t | a |
| 2452: 17183217 | t | c |
| 2453: 17187505 | t | c |
| 2454: 17187608 | t | c |
| 2455: 17187972 | a | c |
| 2456: 17188458 | t | c |
| 2457: 17188792 | g | a |
| 2458: 17189416 | c | t |
| 2459: 17189438 | a | g |
| 2460: 17189954 | t | g |
| 2461: 17190814 | c | t |
| 2462: 17190947 | t | c |
| 2463: 17190955 | a | g |
| 2464: 17191095 | c | t |
| 2465: 17191187 | a | g |
| 2466: 17191319 | a | c |
| 2467: 17191384 | c | t |
| 2468: 17191706 | c | t |
| 2469: 17191828 | c | t |
| 2470: 17191888 | a | g |
| 2471: 17192125 | t | c |
| 2472: 17192155 | t | g |
| 2473: 17192291 | c | t |
| 2474: 17192323 | t | c |
| 2475: 17192740 | a | g |
| 2476: 17192956 | c | a |
| 2477: 17193172 | g | a |
| 2478: 17193312 | g | a |
| 2479: 17193510 | t | c |
| 2480: 17193677 | c | t |
| 2481: 17193691 | t | c |
| 2482: 17194149 | a | g |
| 2483: 17194278 | a | g |
| 2484: 17194541 | a | t |
| 2485: 17194598 | g | a |
| 2486: 17194676 | t | a |
| 2487: 17197658 | a | t |
| 2488: 17197883 | a | t |
| 2489: 17197893 | a | g |
| 2490: 17198390 | g | c |
| 2491: 17198783 | a | t |
| 2492: 17198890 | c | t |
| 2493: 17199459 | g | t |
| 2494: 17200122 | t | a |
| 2495: 17200243 | t | c |
| 2496: 17201223 | a | g |
| 2497: 17201302 | a | g |
| 2498: 17201457 | g | t |
| 2499: 17201481 | a | t |
| 2500: 17201498 | a | g |
| 2501: 17203618 | g | a |
| 2502: 17203703 | t | c |
| 2503: 17203883 | c | t |
| 2504: 17203980 | a | g |
| 2505: 17204040 | a | c |
| 2506: 17204101 | c | t |
| 2507: 17204110 | t | c |
| 2508: 17204266 | t | c |
| 2509: 17204306 | c | t |
| 2510: 17205279 | c | t |
| 2511: 17205400 | t | c |
| 2512: 17206840 | g | a |
| 2513: 17208618 | t | c |
| 2514: 17212158 | t | c |
| 2515: 17212878 | a | g |
| 2516: 17215588 | g | c |
| 2517: 17215665 | g | a |
| 2518: 17215680 | c | a |
| 2519: 17216205 | t | c |
| 2520: 17216359 | g | a |
| 2521: 17216934 | t | c |
| 2522: 17217570 | c | t |
| 2523: 17218235 | c | g |
| 2524: 17218403 | t | g |
| 2525: 17218954 | t | a |
| 2526: 17219093 | t | c |
| 2527: 17219346 | g | a |
| 2528: 17220269 | g | a |
| 2529: 17220847 | t | c |
| 2530: 17222569 | t | c |
| 2531: 17223332 | g | a |
| 2532: 17223513 | c | t |
| 2533: 17223709 | c | a |
| 2534: 17224579 | c | t |
| 2535: 17226514 | c | g |
| 2536: 17229064 | a | g |
| 2537: 17230840 | g | c |
| 2538: 17231154 | t | c |
| 2539: 17233519 | t | c |
| 2540: 17235075 | c | g |
| 2541: 17235409 | a | g |
| 2542: 17237395 | g | a |
| 2543: 17242185 | c | t |
| 2544: 17242365 | g | a |
| 2545: 17242594 | g | a |
| 2546: 17248022 | t | c |
| 2547: 17250853 | c | t |
| 2548: 17256513 | a | c |
| 2549: 17257876 | g | a |
| 2550: 17259371 | t | c |
| 2551: 17259500 | c | t |
| 2552: 17259628 | t | c |
| 2553: 17260102 | a | g |
| 2554: 17260241 | t | c |
| 2555: 17261139 | t | c |
| 2556: 17261763 | a | c |
| 2557: 17262475 | t | g |
| 2558: 17264806 | g | c |
| 2559: 17265142 | t | c |
| 2560: 17267477 | c | t |
| 2561: 17267552 | g | t |
| 2562: 17268277 | c | a |
| 2563: 17270106 | t | c |
| 2564: 17271170 | c | t |
| 2565: 17271348 | c | t |
| 2566: 17271667 | c | t |
| 2567: 17272145 | t | c |
| 2568: 17274570 | t | c |
| 2569: 17278768 | a | c |
| 2570: 17279853 | a | c |
| 2571: 17279857 | c | t |
| 2572: 17280614 | t | c |
| 2573: 17281265 | g | a |
| 2574: 17281678 | t | a |
| 2575: 17283113 | g | a |
| 2576: 17284161 | g | a |
| 2577: 17284210 | c | g |
| 2578: 17284224 | a | t |
| 2579: 17285034 | c | t |
| 2580: 17286397 | g | a |
| 2581: 17286878 | t | c |
| 2582: 17289926 | a | g |
| 2583: 17291405 | t | c |
| 2584: 17291787 | t | c |
| 2585: 17296078 | c | t |
| 2586: 17296288 | t | c |
| 2587: 17296542 | g | a |
| 2588: 17296993 | a | g |
| 2589: 17298981 | t | c |
| 2590: 17299344 | c | g |
| 2591: 17299469 | t | g |
| 2592: 17299764 | t | a |
| 2593: 17300433 | g | c |
| 2594: 17301319 | g | a |
| 2595: 17301393 | t | c |
| 2596: 17301903 | c | g |
| 2597: 17302538 | a | g |
| 2598: 17304049 | t | a |
| 2599: 17304159 | g | a |

TABLE 1-continued

| POSITION | REFERENCE_BASE | ALTERNATE_BASE |
|---|---|---|
| 2600: 17305459 | c | a |
| 2601: 17305460 | g | a |
| 2602: 17305754 | t | c |
| 2603: 17306934 | g | a |
| 2604: 17307063 | c | t |
| 2605: 17308161 | a | c |
| 2606: 17308678 | t | c |
| 2607: 17308976 | t | c |
| 2608: 17309355 | a | c |
| 2609: 17309733 | c | t |
| 2610: 17309800 | t | g |
| 2611: 17310148 | t | g |
| 2612: 17310468 | t | c |
| 2613: 17312738 | c | t |
| 2614: 17314415 | t | c |
| 2615: 17315067 | a | t |
| 2616: 17315172 | c | t |
| 2617: 17315393 | t | c |
| 2618: 17315412 | g | t |
| 2619: 17319497 | c | t |
| 2620: 17319817 | a | t |
| 2621: 17333207 | a | g |
| 2622: 17334125 | c | g |
| 2623: 17335034 | g | a |
| 2624: 17335745 | t | a |
| 2625: 17335812 | a | g |
| 2626: 17336873 | a | c |
| 2627: 17337652 | g | a |
| 2628: 17338111 | t | g |
| 2629: 17338519 | c | t |
| 2630: 17343693 | c | t |
| 2631: 17348078 | g | a |
| 2632: 17349106 | a | g |
| 2633: 17349377 | t | c |
| 2634: 17352649 | t | g |
| 2635: 17356282 | t | c |
| 2636: 17363052 | g | c |
| 2637: 17365851 | c | t |
| 2638: 17371088 | a | c |
| 2639: 17372824 | g | a |
| 2640: 17373129 | g | c |
| 2641: 17377569 | t | c |
| 2642: 17379916 | c | t |
| 2643: 17380377 | t | a |
| 2644: 17380405 | g | a |
| 2645: 17381259 | c | a |
| 2646: 17381834 | t | g |
| 2647: 17383082 | a | g |
| 2648: 17383678 | a | g |
| 2649: 17383881 | t | c |
| 2650: 17383912 | a | g |
| 2651: 17387175 | t | c |
| 2652: 17387482 | t | c |
| 2653: 17388561 | a | g |
| 2654: 17389478 | c | a |
| 2655: 17391752 | c | t |
| 2656: 17391802 | a | g |
| 2657: 17391871 | g | a |
| 2658: 17393429 | g | a |
| 2659: 17393555 | a | c |
| 2660: 17394766 | a | t |
| 2661: 17395232 | a | c |
| 2662: 17395400 | g | a |
| 2663: 17396082 | t | a |
| 2664: 17397155 | t | c |
| 2665: 17400564 | g | c |
| 2666: 17402221 | t | c |
| 2667: 17402486 | t | a |
| 2668: 17402706 | t | c |
| 2669: 17403422 | g | a |
| 2670: 17403569 | t | c |
| 2671: 17407971 | t | a |
| 2672: 17408763 | c | t |
| 2673: 17409076 | t | c |
| 2674: 17410171 | c | t |
| 2675: 17410367 | g | a |
| 2676: 17410479 | a | t |
| 2677: 17410778 | a | g |
| 2678: 17412072 | t | g |
| 2679: 17412874 | c | g |
| 2680: 17413782 | g | a |
| 2681: 17415789 | a | c |
| 2682: 17416338 | t | c |
| 2683: 17416942 | c | t |
| 2684: 17417116 | a | t |
| 2685: 17417216 | c | t |
| 2686: 17417458 | c | t |
| 2687: 17419421 | a | g |
| 2688: 17422486 | c | g |
| 2689: 17422680 | g | a |
| 2690: 17425052 | g | t |
| 2691: 17425744 | g | t |
| 2692: 17427232 | g | a |
| 2693: 17428886 | c | t |
| 2694: 17431749 | t | a |
| 2695: 17432007 | c | g |
| 2696: 17438436 | c | t |
| 2697: 17438615 | t | c |
| 2698: 17438849 | a | g |
| 2699: 17440553 | g | c |
| 2700: 17440770 | t | c |
| 2701: 17442496 | t | c |
| 2702: 17442886 | a | g |
| 2703: 17444799 | t | g |
| 2704: 17447422 | a | c |
| 2705: 17448013 | a | g |
| 2706: 17449885 | a | g |
| 2707: 17454102 | t | c |
| 2708: 17459309 | g | a |
| 2709: 17459622 | a | g |
| 2710: 17459786 | a | g |
| 2711: 17461195 | t | g |
| 2712: 17464114 | c | t |
| 2713: 17464234 | c | g |
| 2714: 17467021 | a | t |
| 2715: 17467646 | g | a |
| 2716: 17468714 | g | c |
| 2717: 17469263 | c | t |
| 2718: 17469937 | a | g |
| 2719: 17473605 | c | t |
| 2720: 17473655 | c | t |
| 2721: 17473665 | a | t |
| 2722: 17476466 | a | g |
| 2723: 17477487 | c | g |
| 2724: 17483080 | g | a |
| 2725: 17488365 | t | a |
| 2726: 17506367 | c | t |
| 2727: 17509277 | t | c |
| 2728: 17509402 | a | g |
| 2729: 17509738 | g | a |
| 2730: 17510432 | g | a |
| 2731: 17510712 | t | c |
| 2732: 17512367 | g | a |
| 2733: 17513682 | t | c |
| 2734: 17513717 | t | c |
| 2735: 17513805 | a | g |
| 2736: 17514142 | a | g |
| 2737: 17514374 | g | a |
| 2738: 17515443 | a | c |
| 2739: 17516105 | a | g |
| 2740: 17516225 | a | g |
| 2741: 17516513 | c | g |
| 2742: 17517387 | g | a |
| 2743: 17517712 | t | c |
| 2744: 17517829 | c | t |
| 2745: 17521626 | t | c |
| 2746: 17521840 | t | c |
| 2747: 17521936 | t | a |
| 2748: 17522729 | c | t |
| 2749: 17524342 | c | a |
| 2750: 17526995 | c | t |
| 2751: 17527822 | g | a |
| 2752: 17528701 | c | t |
| 2753: 17528981 | a | g |

TABLE 1-continued

| POSITION | REFERENCE_BASE | ALTERNATE_BASE |
|---|---|---|
| 2754: 17532497 | c | a |
| 2755: 17536364 | g | a |
| 2756: 17536385 | c | t |
| 2757: 17539592 | a | t |
| 2758: 17549846 | c | t |
| 2759: 17550048 | c | g |
| 2760: 17550111 | c | t |
| 2761: 17550222 | t | a |
| 2762: 17550391 | c | t |
| 2763: 17550610 | g | c |
| 2764: 17551171 | t | c |
| 2765: 17551333 | t | c |
| 2766: 17552369 | a | g |
| 2767: 17557676 | t | a |
| 2768: 17559322 | c | a |
| 2769: 17559640 | c | t |
| 2770: 17562208 | g | c |
| 2771: 17564241 | c | a |
| 2772: 17564731 | c | t |
| 2773: 17565826 | t | c |
| 2774: 17569570 | a | g |
| 2775: 17571660 | c | g |
| 2776: 17572368 | g | a |
| 2777: 17572814 | g | a |
| 2778: 17576282 | g | a |
| 2779: 17577520 | g | a |
| 2780: 17578871 | t | g |
| 2781: 17580257 | c | t |
| 2782: 17580288 | t | c |
| 2783: 17581052 | t | c |
| 2784: 17585038 | t | c |
| 2785: 17585627 | c | t |
| 2786: 17587414 | c | t |
| 2787: 17590718 | a | c |
| 2788: 17591876 | t | c |
| 2789: 17593883 | t | c |
| 2790: 17594527 | c | t |
| 2791: 17595240 | a | g |
| 2792: 17596333 | a | g |
| 2793: 17597081 | a | g |
| 2794: 17597473 | t | c |
| 2795: 17602743 | g | a |
| 2796: 17602898 | g | a |
| 2797: 17611242 | c | t |
| 2798: 17612456 | c | t |
| 2799: 17613247 | a | g |
| 2800: 17613620 | t | c |
| 2801: 17613686 | t | c |
| 2802: 17614407 | t | c |
| 2803: 17614736 | g | a |
| 2804: 17625088 | a | g |
| 2805: 17626993 | c | t |
| 2806: 17629231 | g | a |
| 2807: 17631211 | t | g |
| 2808: 17631527 | t | c |
| 2809: 17633594 | g | a |
| 2810: 17634884 | g | a |
| 2811: 17635348 | t | g |
| 2812: 17635522 | g | a |
| 2813: 17637920 | t | c |
| 2814: 17643762 | g | a |
| 2815: 17644672 | t | c |
| 2816: 17645925 | c | t |
| 2817: 17646135 | c | t |
| 2818: 17646248 | t | a |
| 2819: 17646326 | a | g |
| 2820: 17646546 | g | a |
| 2821: 17647096 | g | c |
| 2822: 17647216 | g | a |
| 2823: 17647454 | c | t |
| 2824: 17650077 | c | g |
| 2825: 17651490 | g | t |
| 2826: 17651754 | g | a |
| 2827: 17652168 | g | a |
| 2828: 17652686 | g | c |
| 2829: 17653308 | a | g |
| 2830: 17653504 | a | g |
| 2831: 17656784 | t | c |
| 2832: 17656858 | g | a |
| 2833: 17657525 | c | t |
| 2834: 17657674 | g | t |
| 2835: 17658409 | g | a |
| 2836: 17659415 | g | c |
| 2837: 17661175 | c | t |
| 2838: 17662776 | g | a |
| 2839: 17662960 | a | g |
| 2840: 17663029 | g | t |
| 2841: 17663410 | c | t |
| 2842: 17663451 | g | a |
| 2843: 17663486 | g | t |
| 2844: 17663630 | c | g |
| 2845: 17664261 | t | c |
| 2846: 17664468 | t | c |
| 2847: 17664542 | c | t |
| 2848: 17664602 | c | t |
| 2849: 17665201 | g | a |
| 2850: 17666081 | g | a |
| 2851: 17666248 | t | c |
| 2852: 17666315 | a | g |
| 2853: 17666711 | a | g |
| 2854: 17667126 | c | a |
| 2855: 17667543 | a | t |
| 2856: 17667614 | c | t |
| 2857: 17668434 | a | t |
| 2858: 17668940 | g | t |
| 2859: 17669504 | t | c |
| 2860: 17669574 | a | g |
| 2861: 17670408 | t | c |
| 2862: 17670474 | g | a |
| 2863: 17670565 | a | g |
| 2864: 17671157 | g | t |
| 2865: 17671427 | g | a |
| 2866: 17671898 | a | g |
| 2867: 17673118 | g | t |
| 2868: 17673199 | a | t |
| 2869: 17673446 | t | c |
| 2870: 17673674 | c | t |
| 2871: 17673832 | t | c |
| 2872: 17675317 | g | a |
| 2873: 17676331 | g | c |
| 2874: 17676441 | g | a |
| 2875: 17680205 | g | a |
| 2876: 17680298 | c | t |
| 2877: 17680378 | g | c |
| 2878: 17680484 | t | c |
| 2879: 17680600 | g | a |
| 2880: 17680841 | a | g |
| 2881: 17680997 | a | g |
| 2882: 17681574 | t | c |
| 2883: 17682962 | c | g |
| 2884: 17683317 | c | a |
| 2885: 17683766 | c | a |
| 2886: 17684178 | a | c |
| 2887: 17684698 | t | g |
| 2888: 17684742 | c | a |
| 2889: 17684934 | c | g |
| 2890: 17685171 | g | c |
| 2891: 17685301 | c | t |
| 2892: 17686696 | a | t |
| 2893: 17688714 | g | a |
| 2894: 17688720 | a | g |
| 2895: 17694577 | a | t |
| 2896: 17694726 | c | g |
| 2897: 17696863 | c | a |
| 2898: 17698651 | t | c |
| 2899: 17699827 | c | a |
| 2900: 17705794 | a | t |
| 2901: 17709695 | g | a |
| 2902: 17720429 | a | c |
| 2903: 17721954 | t | c |
| 2904: 17725315 | a | g |
| 2905: 17727405 | c | g |
| 2906: 17730562 | a | g |
| 2907: 17736986 | c | t |

TABLE 1-continued

| | POSITION | REFERENCE_BASE | ALTERNATE_BASE |
|---|---|---|---|
| 2908: | 17737860 | c | t |
| 2909: | 17742267 | a | g |
| 2910: | 17742564 | c | t |
| 2911: | 17743316 | g | a |
| 2912: | 17745189 | a | g |
| 2913: | 17745881 | c | a |
| 2914: | 17747070 | c | g |
| 2915: | 17749146 | t | c |
| 2916: | 17749218 | c | a |
| 2917: | 17756821 | a | g |
| 2918: | 17758061 | a | c |
| 2919: | 17760702 | g | a |
| 2920: | 17760780 | t | g |
| 2921: | 17760976 | a | g |
| 2922: | 17761185 | a | t |
| 2923: | 17761794 | g | a |
| 2924: | 17761811 | t | g |
| 2925: | 17762567 | c | t |
| 2926: | 17762975 | c | t |
| 2927: | 17763485 | g | a |
| 2928: | 17764149 | t | c |
| 2929: | 17764437 | a | t |
| 2930: | 17768287 | t | a |
| 2931: | 17771739 | a | g |
| 2932: | 17771809 | c | t |
| 2933: | 17773064 | c | t |
| 2934: | 17773377 | g | a |
| 2935: | 17775884 | t | c |
| 2936: | 17775964 | g | a |
| 2937: | 17777678 | a | c |
| 2938: | 17778812 | t | a |
| 2939: | 17779980 | c | t |
| 2940: | 17781053 | a | g |
| 2941: | 17788387 | a | t |
| 2942: | 17788484 | g | c |
| 2943: | 17791361 | a | g |
| 2944: | 17792413 | c | a |
| 2945: | 17794602 | t | c |
| 2946: | 17795187 | t | g |
| 2947: | 17795652 | a | c |
| 2948: | 17795980 | g | a |
| 2949: | 17796086 | t | c |
| 2950: | 17796688 | t | c |
| 2951: | 17796764 | a | g |
| 2952: | 17796795 | c | t |
| 2953: | 17797812 | g | a |
| 2954: | 17799562 | t | c |
| 2955: | 17799732 | c | t |
| 2956: | 17800578 | c | t |
| 2957: | 17800679 | t | c |
| 2958: | 17803511 | c | t |
| 2959: | 17804498 | a | g |
| 2960: | 17810832 | c | t |
| 2961: | 17812485 | c | t |
| 2962: | 17819555 | t | a |
| 2963: | 17824538 | t | c |
| 2964: | 17828380 | c | t |
| 2965: | 17833406 | a | g |
| 2966: | 17833983 | c | t |
| 2967: | 17835269 | t | c |
| 2968: | 17836520 | g | a |
| 2969: | 17836781 | c | g |
| 2970: | 17841917 | t | c |
| 2971: | 17843934 | t | c |
| 2972: | 17844423 | c | g |
| 2973: | 17847113 | a | g |
| 2974: | 17850031 | g | a |
| 2975: | 17852052 | c | g |
| 2976: | 17855415 | c | t |
| 2977: | 17858294 | a | c |
| 2978: | 17864141 | g | t |
| 2979: | 17865880 | a | g |
| 2980: | 17867102 | a | g |
| 2981: | 17872103 | c | t |
| 2982: | 17872957 | t | c |
| 2983: | 17873857 | a | c |
| 2984: | 17885094 | c | g |
| 2985: | 17887099 | t | c |
| 2986: | 17888521 | t | c |
| 2987: | 17902559 | c | a |
| 2988: | 17902569 | a | g |
| 2989: | 17902876 | g | a |
| 2990: | 17903104 | g | a |
| 2991: | 17903222 | c | t |
| 2992: | 17903743 | t | a |
| 2993: | 17903827 | t | c |
| 2994: | 17904859 | t | c |
| 2995: | 17905021 | g | a |
| 2996: | 17905668 | a | t |
| 2997: | 17905975 | c | g |
| 2998: | 17908674 | g | t |
| 2999: | 17909256 | t | c |
| 3000: | 17911473 | c | a |
| 3001: | 17911594 | c | g |
| 3002: | 17912462 | t | g |
| 3003: | 17912827 | t | c |
| 3004: | 17912924 | c | t |
| 3005: | 17913950 | a | g |
| 3006: | 17914144 | t | c |
| 3007: | 17915236 | c | t |
| 3008: | 17920938 | g | a |
| 3009: | 17921268 | c | t |
| 3010: | 17921350 | t | c |
| 3011: | 17921369 | c | t |
| 3012: | 17933425 | c | t |
| 3013: | 17935057 | c | t |
| 3014: | 17935888 | c | t |
| 3015: | 17937617 | c | g |
| 3016: | 17938723 | a | c |
| 3017: | 17939084 | g | a |
| 3018: | 17939115 | t | c |
| 3019: | 17939742 | a | g |
| 3020: | 17939986 | c | a |
| 3021: | 17941403 | g | c |
| 3022: | 17941840 | t | c |
| 3023: | 17942620 | g | a |
| 3024: | 17943731 | t | g |
| 3025: | 17943777 | t | c |
| 3026: | 17955426 | t | c |
| 3027: | 17956818 | a | g |
| 3028: | 17966204 | c | t |
| 3029: | 17968513 | c | g |
| 3030: | 17969043 | a | g |
| 3031: | 17969075 | g | t |
| 3032: | 17970354 | c | t |
| 3033: | 17972629 | a | g |
| 3034: | 17973274 | g | a |
| 3035: | 17974892 | g | t |
| 3036: | 17978997 | g | a |
| 3037: | 17983505 | g | a |
| 3038: | 17983822 | c | t |
| 3039: | 17987325 | a | g |
| 3040: | 17988096 | t | c |
| 3041: | 17991260 | t | c |
| 3042: | 17991844 | g | a |
| 3043: | 17991933 | c | a |
| 3044: | 17991961 | t | g |
| 3045: | 17992340 | c | t |
| 3046: | 17992669 | c | t |
| 3047: | 17994812 | g | c |
| 3048: | 17995075 | t | c |
| 3049: | 17995757 | a | g |
| 3050: | 17996222 | c | t |
| 3051: | 17996520 | t | g |
| 3052: | 17997406 | g | c |
| 3053: | 17998464 | a | c |
| 3054: | 17999408 | g | t |
| 3055: | 17999483 | a | c |
| 3056: | 17999616 | g | a |
| 3057: | 17999790 | a | g |
| 3058: | 18000063 | c | t |
| 3059: | 18000103 | t | c |
| 3060: | 18000178 | g | a |
| 3061: | 18001339 | g | a |

TABLE 1-continued

| POSITION | REFERENCE_BASE | ALTERNATE_BASE |
|---|---|---|
| 3062: 18001405 | t | c |
| 3063: 18002501 | c | t |
| 3064: 18003768 | a | g |
| 3065: 18004013 | a | c |
| 3066: 18004040 | t | c |
| 3067: 18004202 | g | t |
| 3068: 18004308 | c | t |
| 3069: 18004507 | c | t |
| 3070: 18004554 | a | t |
| 3071: 18004573 | t | c |
| 3072: 18004627 | g | a |
| 3073: 18004806 | a | g |
| 3074: 18004945 | c | t |
| 3075: 18004989 | g | a |
| 3076: 18005122 | c | t |
| 3077: 18005896 | t | c |
| 3078: 18006127 | t | c |
| 3079: 18006206 | a | g |
| 3080: 18006260 | g | t |
| 3081: 18006365 | t | c |
| 3082: 18006954 | c | t |
| 3083: 18007031 | c | t |
| 3084: 18007042 | a | g |
| 3085: 18007187 | t | c |
| 3086: 18007515 | a | g |
| 3087: 18007521 | a | t |
| 3088: 18007703 | a | g |
| 3089: 18007737 | c | t |
| 3090: 18007825 | g | a |
| 3091: 18011843 | a | c |
| 3092: 18021152 | a | g |
| 3093: 18021191 | g | a |
| 3094: 18021303 | g | a |
| 3095: 18021524 | a | c |
| 3096: 18022707 | a | t |
| 3097: 18025392 | g | a |
| 3098: 18030997 | t | c |
| 3099: 18033814 | g | a |
| 3100: 18033962 | g | a |
| 3101: 18064060 | c | t |
| 3102: 18064455 | c | t |
| 3103: 18064623 | c | t |
| 3104: 18066263 | a | g |
| 3105: 18066463 | c | t |
| 3106: 18066998 | c | t |
| 3107: 18067103 | t | a |
| 3108: 18067290 | g | a |
| 3109: 18069198 | t | c |
| 3110: 18069910 | g | a |
| 3111: 18070164 | g | a |
| 3112: 18072572 | g | a |
| 3113: 18072925 | t | c |
| 3114: 18074338 | c | t |
| 3115: 18074380 | a | c |
| 3116: 18074455 | c | t |
| 3117: 18075694 | g | a |
| 3118: 18076179 | a | g |
| 3119: 18076283 | a | g |
| 3120: 18076338 | g | a |
| 3121: 18080048 | a | g |
| 3122: 18081695 | a | g |
| 3123: 18082352 | c | t |
| 3124: 18083163 | t | c |
| 3125: 18084356 | c | t |
| 3126: 18086551 | a | g |
| 3127: 18086717 | c | t |
| 3128: 18087120 | a | g |
| 3129: 18087431 | t | c |
| 3130: 18087675 | c | t |
| 3131: 18087828 | g | t |
| 3132: 18087883 | a | g |
| 3133: 18088892 | a | g |
| 3134: 18089833 | t | c |
| 3135: 18090029 | a | g |
| 3136: 18091780 | a | g |
| 3137: 18093344 | c | t |
| 3138: 18094667 | g | t |
| 3139: 18098102 | t | c |
| 3140: 18102051 | g | a |
| 3141: 18103547 | c | g |
| 3142: 18103621 | t | a |
| 3143: 18105666 | a | g |
| 3144: 18112452 | a | g |
| 3145: 18113119 | g | a |
| 3146: 18114308 | g | a |
| 3147: 18125288 | t | c |
| 3148: 18129336 | g | a |
| 3149: 18134303 | g | c |
| 3150: 18137041 | g | t |
| 3151: 18138481 | g | a |
| 3152: 18138871 | a | g |
| 3153: 18141716 | g | c |
| 3154: 18142013 | t | c |
| 3155: 18142482 | a | g |
| 3156: 18142498 | g | a |
| 3157: 18143539 | a | g |
| 3158: 18144507 | g | a |
| 3159: 18146381 | a | g |
| 3160: 18147285 | a | g |
| 3161: 18147368 | g | a |
| 3162: 18147479 | t | g |
| 3163: 18147849 | t | g |
| 3164: 18148090 | a | g |
| 3165: 18148391 | g | t |
| 3166: 18149727 | a | t |
| 3167: 18162515 | c | t |
| 3168: 18167850 | a | c |
| 3169: 18169299 | c | t |
| 3170: 18170395 | g | a |

TABLE 2

| POSITION | REFERENCE_BASE | ALTERNATE_BASE |
|---|---|---|
| 1: 13786332 | g | c |
| 2: 13789552 | t | c |
| 3: 13794088 | g | t |
| 4: 13795042 | t | g |
| 5: 13795784 | g | c |
| 6: 13798031 | a | g |
| 7: 13798945 | g | a |
| 8: 13808775 | g | t |
| 9: 13810343 | t | a |
| 10: 13845012 | t | g |
| 11: 13857670 | t | a |
| 12: 13863248 | a | g |
| 13: 13868547 | c | g |
| 14: 13871664 | g | a |
| 15: 13872007 | t | g |
| 16: 13944350 | t | a |
| 17: 13946958 | c | t |
| 18: 13952218 | g | a |
| 19: 13952240 | c | t |
| 20: 13953249 | c | t |
| 21: 13955300 | a | g |
| 22: 13955542 | a | g |
| 23: 13957524 | c | t |
| 24: 13969607 | g | a |
| 25: 13989352 | c | t |
| 26: 13991942 | t | c |
| 27: 13994180 | a | g |
| 28: 13998796 | c | t |
| 29: 14012310 | a | c |
| 30: 14022029 | c | t |
| 31: 14055038 | g | a |
| 32: 14056661 | a | g |
| 33: 14057058 | c | t |
| 34: 14057841 | a | g |
| 35: 14063842 | t | c |
| 36: 14064036 | a | g |
| 37: 14065022 | a | c |

TABLE 2-continued

| | POSITION | REFERENCE_BASE | ALTERNATE_BASE |
|---|---|---|---|
| 38: | 14065054 | a | g |
| 39: | 14072304 | t | c |
| 40: | 14077207 | c | t |
| 41: | 14089145 | t | c |
| 42: | 14092446 | c | t |
| 43: | 14109164 | t | c |
| 44: | 14136408 | t | a |
| 45: | 14152957 | a | g |
| 46: | 14154909 | c | t |
| 47: | 14163567 | g | c |
| 48: | 14202814 | a | g |
| 49: | 14202816 | g | a |
| 50: | 14203860 | t | c |
| 51: | 14227826 | c | t |
| 52: | 14233001 | g | t |
| 53: | 14246775 | a | g |
| 54: | 14249388 | g | a |
| 55: | 14251065 | g | c |
| 56: | 14253526 | t | c |
| 57: | 14282614 | c | t |
| 58: | 14289973 | g | t |
| 59: | 14303801 | a | t |
| 60: | 14305564 | g | a |
| 61: | 14308745 | a | g |
| 62: | 14309271 | g | a |
| 63: | 14313634 | c | a |
| 64: | 14316517 | t | c |
| 65: | 14336497 | a | g |
| 66: | 14337704 | t | c |
| 67: | 14341977 | c | g |
| 68: | 14344127 | a | c |
| 69: | 14344521 | t | g |
| 70: | 14347249 | c | t |
| 71: | 14348761 | g | a |
| 72: | 14356012 | t | g |
| 73: | 14357072 | t | g |
| 74: | 14368727 | c | t |
| 75: | 14380858 | c | t |
| 76: | 14381653 | a | g |
| 77: | 14412471 | g | c |
| 78: | 14443836 | c | a |
| 79: | 14450249 | t | a |
| 80: | 14523926 | a | g |
| 81: | 14529213 | t | c |
| 82: | 14560271 | g | a |
| 83: | 14591293 | g | a |
| 84: | 14601683 | t | c |
| 85: | 14614643 | t | c |
| 86: | 14627536 | c | a |
| 87: | 14639294 | c | t |
| 88: | 14639798 | c | t |
| 89: | 14666163 | t | c |
| 90: | 14686785 | c | t |
| 91: | 14778389 | t | a |
| 92: | 14791193 | t | g |
| 93: | 14806046 | t | g |
| 94: | 14808476 | a | g |
| 95: | 14808794 | g | a |
| 96: | 14809810 | c | t |
| 97: | 14809974 | c | t |
| 98: | 14814482 | g | a |
| 99: | 14814537 | t | a |
| 100: | 14823503 | g | t |
| 101: | 14825824 | t | c |
| 102: | 14826425 | g | a |
| 103: | 14827550 | c | t |
| 104: | 14834456 | c | g |
| 105: | 14842048 | t | c |
| 106: | 14886344 | g | t |
| 107: | 14890054 | a | c |
| 108: | 14892017 | c | t |
| 109: | 14892649 | c | t |
| 110: | 14900671 | a | t |
| 111: | 14945268 | t | c |
| 112: | 14946296 | a | g |
| 113: | 14951614 | a | g |
| 114: | 14951808 | c | g |
| 115: | 14957690 | c | a |
| 116: | 14965613 | c | t |
| 117: | 14970970 | g | a |
| 118: | 14999022 | g | a |
| 119: | 14999072 | a | c |
| 120: | 14999132 | t | g |
| 121: | 14999231 | a | g |
| 122: | 14999774 | c | t |
| 123: | 14999842 | t | g |
| 124: | 15000185 | c | a |
| 125: | 15000225 | t | a |
| 126: | 15000615 | g | a |
| 127: | 15000928 | g | c |
| 128: | 15001303 | c | t |
| 129: | 15001357 | a | c |
| 130: | 15001514 | c | g |
| 131: | 15001760 | g | a |
| 132: | 15001785 | g | a |
| 133: | 15001983 | a | g |
| 134: | 15002044 | c | t |
| 135: | 15002118 | t | c |
| 136: | 15002260 | g | c |
| 137: | 15002436 | g | c |
| 138: | 15002447 | a | g |
| 139: | 15002601 | a | g |
| 140: | 15002681 | a | g |
| 141: | 15003106 | c | g |
| 142: | 15003363 | g | t |
| 143: | 15003544 | c | a |
| 144: | 15003596 | t | c |
| 145: | 15003973 | g | t |
| 146: | 15004000 | c | t |
| 147: | 15004200 | g | a |
| 148: | 15004222 | t | g |
| 149: | 15004468 | t | c |
| 150: | 15004577 | g | a |
| 151: | 15004725 | a | t |
| 152: | 15004739 | t | c |
| 153: | 15004935 | g | c |
| 154: | 15004988 | c | t |
| 155: | 15005084 | g | a |
| 156: | 15005148 | a | g |
| 157: | 15005159 | a | g |
| 158: | 15005540 | g | a |
| 159: | 15025974 | t | c |
| 160: | 15026705 | a | c |
| 161: | 15048712 | a | g |
| 162: | 15087229 | g | a |
| 163: | 15115597 | c | a |
| 164: | 15141829 | a | g |
| 165: | 15143231 | g | a |
| 166: | 15210898 | g | t |
| 167: | 15232784 | c | t |
| 168: | 15249147 | t | a |
| 169: | 15286306 | t | c |
| 170: | 15298032 | t | c |
| 171: | 15299313 | g | t |
| 172: | 15335133 | c | t |
| 173: | 15351079 | a | t |
| 174: | 15362167 | t | g |
| 175: | 15370212 | a | g |
| 176: | 15373919 | t | c |
| 177: | 15374182 | a | g |
| 178: | 15375609 | a | t |
| 179: | 15376324 | t | a |
| 180: | 15395417 | t | c |
| 181: | 15399434 | c | t |
| 182: | 15414814 | a | t |
| 183: | 15423539 | t | c |
| 184: | 15424699 | a | t |
| 185: | 15427464 | t | g |
| 186: | 15435332 | t | c |
| 187: | 15437951 | a | g |
| 188: | 15438194 | t | c |
| 189: | 15453738 | a | c |
| 190: | 15471061 | t | c |
| 191: | 15522640 | a | c |

TABLE 2-continued

| | POSITION | REFERENCE_BASE | ALTERNATE_BASE |
|---|---|---|---|
| 192: | 15553225 | a | g |
| 193: | 15555505 | c | t |
| 194: | 15565145 | a | g |
| 195: | 15617474 | t | c |
| 196: | 15642114 | a | g |
| 197: | 15679735 | t | g |
| 198: | 15696652 | t | c |
| 199: | 15708909 | t | c |
| 200: | 15711358 | g | a |
| 201: | 15742331 | t | c |
| 202: | 15745340 | c | g |
| 203: | 15792778 | c | t |
| 204: | 15809741 | a | g |
| 205: | 15813986 | c | t |
| 206: | 15814037 | a | g |
| 207: | 15815872 | g | a |
| 208: | 15815917 | t | c |
| 209: | 15817984 | t | c |
| 210: | 15818374 | a | g |
| 211: | 15849570 | a | c |
| 212: | 15857950 | a | t |
| 213: | 15865992 | t | a |
| 214: | 15881133 | g | c |
| 215: | 15887520 | t | c |
| 216: | 15895527 | g | c |
| 217: | 15903809 | a | t |
| 218: | 15922876 | g | a |
| 219: | 15937899 | c | t |
| 220: | 15949824 | c | t |
| 221: | 15954079 | t | c |
| 222: | 15955158 | a | g |
| 223: | 15970406 | t | c |
| 224: | 15978044 | g | a |
| 225: | 16029704 | a | g |
| 226: | 16030927 | t | c |
| 227: | 16035195 | a | g |
| 228: | 16038904 | g | c |
| 229: | 16056870 | c | t |
| 230: | 16094042 | t | g |
| 231: | 16094737 | a | t |
| 232: | 16104503 | c | t |
| 233: | 16161202 | c | t |
| 234: | 16168166 | c | g |
| 235: | 16171036 | g | a |
| 236: | 16173907 | t | g |
| 237: | 16193590 | a | g |
| 238: | 16217867 | t | c |
| 239: | 16238199 | c | t |
| 240: | 16243372 | a | t |
| 241: | 16274234 | a | g |
| 242: | 16317969 | a | g |
| 243: | 16327992 | g | c |
| 244: | 16337850 | a | t |
| 245: | 16338022 | t | g |
| 246: | 16360523 | t | c |
| 247: | 16389837 | g | a |
| 248: | 16394347 | t | c |
| 249: | 16394992 | a | g |
| 250: | 16403291 | g | t |
| 251: | 16405553 | a | g |
| 252: | 16429877 | a | g |
| 253: | 16431582 | t | c |
| 254: | 16434635 | a | g |
| 255: | 16437778 | g | t |
| 256: | 16439992 | c | g |
| 257: | 16447097 | t | c |
| 258: | 16491522 | a | g |
| 259: | 16494732 | t | g |
| 260: | 16501248 | a | g |
| 261: | 16508146 | t | c |
| 262: | 16636222 | t | c |
| 263: | 16636797 | c | a |
| 264: | 16686966 | c | t |
| 265: | 16705428 | c | t |
| 266: | 16753307 | a | t |
| 267: | 16757962 | a | g |
| 268: | 16766335 | c | t |
| 269: | 16779020 | a | t |
| 270: | 16784770 | c | t |
| 271: | 16803656 | c | g |
| 272: | 16804768 | g | t |
| 273: | 16853980 | c | t |
| 274: | 16858486 | a | t |
| 275: | 16861847 | c | t |
| 276: | 16865089 | a | c |
| 277: | 16866854 | c | g |
| 278: | 16876526 | t | c |
| 279: | 16883444 | c | t |
| 280: | 16968693 | t | c |
| 281: | 16971929 | a | g |
| 282: | 17021105 | g | a |
| 283: | 17031548 | t | c |
| 284: | 17060994 | t | c |
| 285: | 17064711 | c | t |
| 286: | 17064940 | a | g |
| 287: | 17074484 | c | t |
| 288: | 17088556 | c | t |
| 289: | 17113095 | a | g |
| 290: | 17116558 | a | c |
| 291: | 17120029 | a | g |
| 292: | 17131193 | t | c |
| 293: | 17153912 | a | g |
| 294: | 17167383 | t | c |
| 295: | 17170539 | g | c |
| 296: | 17179698 | a | t |
| 297: | 17193632 | g | a |
| 298: | 17199522 | a | t |
| 299: | 17201025 | t | a |
| 300: | 17207642 | c | t |
| 301: | 17228878 | g | a |
| 302: | 17232783 | a | g |
| 303: | 17233396 | g | a |
| 304: | 17238359 | a | g |
| 305: | 17239125 | g | a |
| 306: | 17243006 | c | t |
| 307: | 17244215 | g | c |
| 308: | 17244585 | g | a |
| 309: | 17245498 | g | c |
| 310: | 17249409 | c | t |
| 311: | 17258945 | g | a |
| 312: | 17259285 | a | g |
| 313: | 17262233 | g | t |
| 314: | 17265233 | g | a |
| 315: | 17267396 | a | t |
| 316: | 17276911 | g | a |
| 317: | 17283143 | g | a |
| 318: | 17287690 | a | t |
| 319: | 17296703 | g | c |
| 320: | 17316277 | g | a |
| 321: | 17322467 | a | c |
| 322: | 17345540 | g | t |
| 323: | 17351785 | a | c |
| 324: | 17381722 | g | a |
| 325: | 17437280 | g | c |
| 326: | 17467870 | t | c |
| 327: | 17468444 | a | g |
| 328: | 17490372 | g | a |
| 329: | 17548337 | g | t |
| 330: | 17615441 | g | c |
| 331: | 17627574 | a | c |
| 332: | 17635725 | a | c |
| 333: | 17645927 | a | g |
| 334: | 17646932 | t | c |
| 335: | 17683823 | t | g |
| 336: | 17711750 | c | g |
| 337: | 17776065 | a | g |
| 338: | 17779015 | a | g |
| 339: | 17819480 | a | g |
| 340: | 17820025 | t | c |
| 341: | 17887100 | t | a |
| 342: | 17902653 | a | t |
| 343: | 17902971 | t | c |
| 344: | 17902973 | a | g |
| 345: | 17975014 | g | c |

TABLE 2-continued

| | POSITION | REFERENCE_BASE | ALTERNATE_BASE |
|---|---|---|---|
| 346: | 18003363 | a | g |
| 347: | 18006481 | a | t |
| 348: | 18015976 | t | c |
| 349: | 18016117 | g | a |
| 350: | 18018984 | t | g |
| 351: | 18022010 | t | c |
| 352: | 18023585 | c | t |
| 353: | 18023870 | g | a |
| 354: | 18025742 | g | c |
| 355: | 18075838 | g | c |
| 356: | 18134065 | c | t |
| 357: | 18151118 | g | a |
| 358: | 18156425 | a | t |
| 359: | 18166871 | g | c |
| 360: | 18167968 | a | g |
| 361: | 18170580 | c | t |

TABLE 3

| | POSITION | REFERENCE_BASE | ALTERNATE_BASE |
|---|---|---|---|
| 1: | 13793202 | c | t |
| 2: | 13795971 | g | a |
| 3: | 13807082 | a | c |
| 4: | 13807169 | t | c |
| 5: | 13807650 | t | c |
| 6: | 13809615 | c | t |
| 7: | 13809703 | c | t |
| 8: | 13812148 | c | t |
| 9: | 13833651 | c | t |
| 10: | 13840293 | c | a |
| 11: | 13851092 | c | t |
| 12: | 13858215 | g | a |
| 13: | 13860247 | c | t |
| 14: | 13861613 | a | g |
| 15: | 13862837 | c | t |
| 16: | 13868013 | c | g |
| 17: | 13868860 | a | g |
| 18: | 13869319 | a | g |
| 19: | 13899997 | c | a |
| 20: | 13901998 | c | g |
| 21: | 13918642 | t | c |
| 22: | 13918743 | g | a |
| 23: | 13925431 | t | g |
| 24: | 13939753 | a | t |
| 25: | 13954707 | a | g |
| 26: | 13968279 | t | c |
| 27: | 13989194 | t | c |
| 28: | 13994402 | a | g |
| 29: | 14027813 | t | c |
| 30: | 14028654 | a | g |
| 31: | 14029967 | a | c |
| 32: | 14031277 | g | a |
| 33: | 14032871 | g | c |
| 34: | 14034217 | g | a |
| 35: | 14034364 | t | c |
| 36: | 14046782 | c | t |
| 37: | 14051729 | t | c |
| 38: | 14052410 | t | c |
| 39: | 14062535 | a | g |
| 40: | 14062927 | c | t |
| 41: | 14065683 | a | c |
| 42: | 14068709 | a | c |
| 43: | 14079109 | a | g |
| 44: | 14089137 | a | c |
| 45: | 14089142 | a | g |
| 46: | 14095378 | a | g |
| 47: | 14109422 | g | a |
| 48: | 14122001 | a | c |
| 49: | 14141359 | a | c |
| 50: | 14142005 | t | g |
| 51: | 14142139 | a | c |
| 52: | 14155080 | a | t |
| 53: | 14201941 | t | g |

TABLE 3-continued

| | POSITION | REFERENCE_BASE | ALTERNATE_BASE |
|---|---|---|---|
| 54: | 14203698 | c | t |
| 55: | 14203930 | a | g |
| 56: | 14204116 | t | c |
| 57: | 14218571 | a | t |
| 58: | 14224397 | t | c |
| 59: | 14228263 | g | c |
| 60: | 14235135 | c | t |
| 61: | 14241206 | c | t |
| 62: | 14244972 | g | a |
| 63: | 14249399 | a | g |
| 64: | 14251146 | g | c |
| 65: | 14251892 | t | c |
| 66: | 14253621 | a | t |
| 67: | 14254529 | t | a |
| 68: | 14277524 | a | g |
| 69: | 14279513 | t | a |
| 70: | 14289715 | t | a |
| 71: | 14290282 | a | g |
| 72: | 14290530 | g | t |
| 73: | 14294997 | t | c |
| 74: | 14295769 | c | t |
| 75: | 14295939 | a | g |
| 76: | 14297189 | t | c |
| 77: | 14299671 | a | g |
| 78: | 14299674 | c | t |
| 79: | 14299711 | t | c |
| 80: | 14300125 | c | t |
| 81: | 14304391 | a | g |
| 82: | 14304642 | t | c |
| 83: | 14307883 | t | c |
| 84: | 14308299 | a | g |
| 85: | 14308460 | g | a |
| 86: | 14310283 | c | t |
| 87: | 14312072 | a | g |
| 88: | 14315594 | t | c |
| 89: | 14325463 | t | g |
| 90: | 14325687 | g | t |
| 91: | 14336793 | g | a |
| 92: | 14351418 | g | a |
| 93: | 14351691 | g | c |
| 94: | 14352181 | c | t |
| 95: | 14354527 | t | c |
| 96: | 14355445 | c | g |
| 97: | 14361735 | g | a |
| 98: | 14362906 | t | c |
| 99: | 14377173 | t | c |
| 100: | 14379074 | a | c |
| 101: | 14379466 | c | t |
| 102: | 14392496 | t | c |
| 103: | 14392568 | g | a |
| 104: | 14395584 | a | c |
| 105: | 14396231 | c | t |
| 106: | 14412774 | a | g |
| 107: | 14424801 | t | c |
| 108: | 14427417 | t | c |
| 109: | 14427482 | g | c |
| 110: | 14440576 | c | a |
| 111: | 14442675 | t | g |
| 112: | 14442719 | t | g |
| 113: | 14444533 | a | g |
| 114: | 14446001 | a | g |
| 115: | 14448003 | t | a |
| 116: | 14449153 | c | t |
| 117: | 14454279 | t | g |
| 118: | 14459068 | c | t |
| 119: | 14464047 | a | t |
| 120: | 14464959 | t | c |
| 121: | 14465766 | t | c |
| 122: | 14475385 | t | c |
| 123: | 14500484 | c | t |
| 124: | 14514847 | c | t |
| 125: | 14520160 | a | t |
| 126: | 14525178 | a | c |
| 127: | 14529211 | c | t |
| 128: | 14532728 | t | c |
| 129: | 14536062 | a | c |
| 130: | 14541497 | a | g |

TABLE 3-continued

| | POSITION | REFERENCE_BASE | ALTERNATE_BASE |
|---|---|---|---|
| 131: | 14544386 | t | c |
| 132: | 14581049 | t | c |
| 133: | 14583783 | c | a |
| 134: | 14584821 | c | g |
| 135: | 14605448 | c | t |
| 136: | 14621113 | t | c |
| 137: | 14621379 | t | a |
| 138: | 14623460 | a | g |
| 139: | 14630525 | a | c |
| 140: | 14630610 | t | g |
| 141: | 14631799 | t | c |
| 142: | 14632590 | t | c |
| 143: | 14641424 | a | t |
| 144: | 14644530 | a | t |
| 145: | 14645138 | c | t |
| 146: | 14646515 | c | t |
| 147: | 14671181 | a | g |
| 148: | 14672513 | t | g |
| 149: | 14673701 | t | c |
| 150: | 14676902 | c | t |
| 151: | 14704141 | t | a |
| 152: | 14708401 | a | g |
| 153: | 14759724 | t | c |
| 154: | 14775795 | c | a |
| 155: | 14778736 | g | a |
| 156: | 14801146 | c | t |
| 157: | 14834449 | c | g |
| 158: | 14836432 | g | a |
| 159: | 14840248 | t | c |
| 160: | 14841901 | g | a |
| 161: | 14842227 | a | c |
| 162: | 14842776 | c | t |
| 163: | 14843263 | c | g |
| 164: | 14886799 | a | g |
| 165: | 14887060 | t | c |
| 166: | 14890588 | g | a |
| 167: | 14892192 | c | t |
| 168: | 14893868 | a | g |
| 169: | 14900711 | t | g |
| 170: | 14901291 | t | a |
| 171: | 14903115 | c | a |
| 172: | 14916672 | t | c |
| 173: | 14920503 | t | a |
| 174: | 14925694 | t | c |
| 175: | 14930044 | g | c |
| 176: | 14930395 | a | c |
| 177: | 14931113 | a | g |
| 178: | 14932380 | c | g |
| 179: | 14937142 | c | t |
| 180: | 14938871 | a | g |
| 181: | 14940266 | t | c |
| 182: | 14945976 | c | t |
| 183: | 14947005 | t | c |
| 184: | 14949091 | a | g |
| 185: | 14952249 | a | c |
| 186: | 14955951 | g | a |
| 187: | 14957355 | c | t |
| 188: | 14957571 | c | t |
| 189: | 14958320 | c | t |
| 190: | 14967763 | a | c |
| 191: | 14968075 | t | a |
| 192: | 14968622 | t | c |
| 193: | 14974256 | a | c |
| 194: | 15000979 | a | g |
| 195: | 15002808 | t | g |
| 196: | 15002869 | c | t |
| 197: | 15003459 | g | a |
| 198: | 15004691 | c | a |
| 199: | 15014070 | t | c |
| 200: | 15018850 | g | a |
| 201: | 15020436 | g | a |
| 202: | 15020440 | a | g |
| 203: | 15056327 | t | c |
| 204: | 15064728 | g | a |
| 205: | 15073139 | t | c |
| 206: | 15078999 | t | c |
| 207: | 15083283 | a | g |
| 208: | 15115316 | c | g |
| 209: | 15115423 | c | a |
| 210: | 15120676 | c | t |
| 211: | 15123388 | g | a |
| 212: | 15130427 | t | a |
| 213: | 15137817 | a | c |
| 214: | 15143098 | c | t |
| 215: | 15143140 | c | a |
| 216: | 15159625 | a | g |
| 217: | 15160203 | c | t |
| 218: | 15167150 | a | g |
| 219: | 15174684 | t | a |
| 220: | 15183225 | c | t |
| 221: | 15183636 | a | t |
| 222: | 15224071 | t | c |
| 223: | 15280085 | t | c |
| 224: | 15281410 | c | t |
| 225: | 15302421 | a | c |
| 226: | 15328920 | a | c |
| 227: | 15328921 | a | t |
| 228: | 15329117 | g | a |
| 229: | 15336885 | t | a |
| 230: | 15340434 | t | c |
| 231: | 15341050 | c | t |
| 232: | 15343408 | g | c |
| 233: | 15349577 | g | a |
| 234: | 15358854 | t | c |
| 235: | 15359010 | c | t |
| 236: | 15360371 | g | a |
| 237: | 15360415 | a | c |
| 238: | 15362712 | a | t |
| 239: | 15369500 | c | t |
| 240: | 15377503 | t | c |
| 241: | 15379111 | a | g |
| 242: | 15381505 | t | c |
| 243: | 15395614 | c | g |
| 244: | 15418140 | t | c |
| 245: | 15427052 | a | g |
| 246: | 15438583 | g | t |
| 247: | 15440219 | a | g |
| 248: | 15450658 | a | g |
| 249: | 15469944 | t | a |
| 250: | 15497208 | t | a |
| 251: | 15529113 | a | g |
| 252: | 15531290 | g | t |
| 253: | 15536720 | a | g |
| 254: | 15555005 | a | c |
| 255: | 15594759 | c | t |
| 256: | 15599617 | c | t |
| 257: | 15601332 | a | g |
| 258: | 15603328 | c | g |
| 259: | 15605767 | a | g |
| 260: | 15642143 | a | g |
| 261: | 15644736 | t | a |
| 262: | 15648823 | c | t |
| 263: | 15650129 | c | t |
| 264: | 15653803 | g | c |
| 265: | 15656922 | c | g |
| 266: | 15663671 | c | a |
| 267: | 15675577 | t | a |
| 268: | 15675976 | t | c |
| 269: | 15676508 | c | t |
| 270: | 15676597 | c | t |
| 271: | 15681214 | t | a |
| 272: | 15682739 | t | g |
| 273: | 15682925 | c | t |
| 274: | 15684253 | t | g |
| 275: | 15687054 | g | a |
| 276: | 15688596 | t | c |
| 277: | 15689303 | a | g |
| 278: | 15692480 | g | a |
| 279: | 15693924 | c | a |
| 280: | 15695029 | g | t |
| 281: | 15707183 | t | c |
| 282: | 15714285 | t | c |
| 283: | 15714774 | g | a |
| 284: | 15716047 | a | c |

TABLE 3-continued

| | POSITION | REFERENCE_BASE | ALTERNATE_BASE |
|---|---|---|---|
| 285: | 15718727 | t | c |
| 286: | 15718927 | g | a |
| 287: | 15721987 | a | g |
| 288: | 15740761 | c | t |
| 289: | 15742761 | c | t |
| 290: | 15743816 | g | a |
| 291: | 15751207 | a | g |
| 292: | 15751246 | a | t |
| 293: | 15751359 | c | t |
| 294: | 15754104 | t | c |
| 295: | 15760186 | c | t |
| 296: | 15769673 | a | g |
| 297: | 15815282 | c | t |
| 298: | 15817939 | g | a |
| 299: | 15833254 | c | a |
| 300: | 15835481 | c | g |
| 301: | 15851711 | c | t |
| 302: | 15852041 | c | g |
| 303: | 15853469 | g | c |
| 304: | 15853824 | a | g |
| 305: | 15869264 | t | c |
| 306: | 15869845 | t | a |
| 307: | 15870773 | a | g |
| 308: | 15872349 | c | g |
| 309: | 15896141 | t | c |
| 310: | 15925924 | t | c |
| 311: | 16029732 | t | c |
| 312: | 16030763 | c | t |
| 313: | 16033046 | g | a |
| 314: | 16044815 | g | t |
| 315: | 16059769 | c | t |
| 316: | 16060265 | c | g |
| 317: | 16063918 | c | t |
| 318: | 16064730 | g | a |
| 319: | 16073916 | g | a |
| 320: | 16074294 | t | c |
| 321: | 16074744 | a | g |
| 322: | 16093631 | c | t |
| 323: | 16100689 | t | g |
| 324: | 16107592 | t | g |
| 325: | 16124106 | a | g |
| 326: | 16131138 | t | c |
| 327: | 16131244 | c | a |
| 328: | 16134155 | a | g |
| 329: | 16137958 | c | t |
| 330: | 16139214 | g | a |
| 331: | 16140602 | a | g |
| 332: | 16140671 | g | t |
| 333: | 16140703 | t | g |
| 334: | 16163942 | g | t |
| 335: | 16167455 | g | a |
| 336: | 16172690 | t | a |
| 337: | 16184901 | c | t |
| 338: | 16185389 | a | g |
| 339: | 16187994 | a | g |
| 340: | 16293656 | g | c |
| 341: | 16305378 | a | g |
| 342: | 16313571 | a | g |
| 343: | 16336578 | g | a |
| 344: | 16360879 | c | g |
| 345: | 16423969 | a | t |
| 346: | 16423970 | a | t |
| 347: | 16423976 | c | g |
| 348: | 16431541 | g | c |
| 349: | 16448336 | c | g |
| 350: | 16452007 | a | c |
| 351: | 16453773 | a | c |
| 352: | 16457724 | c | t |
| 353: | 16490654 | t | g |
| 354: | 16495290 | c | t |
| 355: | 16540260 | t | c |
| 356: | 16544023 | c | a |
| 357: | 16556486 | t | a |
| 358: | 16559936 | c | t |
| 359: | 16561463 | a | c |
| 360: | 16561464 | a | g |
| 361: | 16570267 | c | a |
| 362: | 16583160 | a | g |
| 363: | 16595038 | t | a |
| 364: | 16649623 | t | a |
| 365: | 16663333 | g | a |
| 366: | 16704084 | c | g |
| 367: | 16721418 | a | t |
| 368: | 16724279 | c | g |
| 369: | 16727706 | c | a |
| 370: | 16728251 | a | g |
| 371: | 16743202 | a | t |
| 372: | 16745378 | a | g |
| 373: | 16751447 | g | a |
| 374: | 16789636 | g | a |
| 375: | 16791935 | a | g |
| 376: | 16797023 | a | c |
| 377: | 16799064 | c | t |
| 378: | 16799466 | g | a |
| 379: | 16804904 | c | t |
| 380: | 16807655 | c | t |
| 381: | 16808954 | a | g |
| 382: | 16812750 | a | g |
| 383: | 16818812 | t | a |
| 384: | 16822411 | a | t |
| 385: | 16834673 | a | t |
| 386: | 16836920 | c | g |
| 387: | 16842646 | c | t |
| 388: | 16846455 | g | c |
| 389: | 16846953 | c | t |
| 390: | 16865096 | c | g |
| 391: | 16872214 | a | t |
| 392: | 16886895 | t | c |
| 393: | 16930714 | t | c |
| 394: | 16943697 | g | a |
| 395: | 16962917 | g | a |
| 396: | 16979427 | a | g |
| 397: | 17004744 | a | t |
| 398: | 17047704 | g | a |
| 399: | 17085341 | c | t |
| 400: | 17096273 | t | c |
| 401: | 17103628 | g | a |
| 402: | 17108144 | g | a |
| 403: | 17119306 | g | a |
| 404: | 17129314 | g | a |
| 405: | 17129588 | a | c |
| 406: | 17131642 | g | a |
| 407: | 17164499 | a | g |
| 408: | 17165382 | t | g |
| 409: | 17167672 | a | g |
| 410: | 17174469 | a | t |
| 411: | 17178186 | a | g |
| 412: | 17180133 | g | a |
| 413: | 17182569 | t | c |
| 414: | 17186173 | t | c |
| 415: | 17187712 | g | a |
| 416: | 17193070 | c | t |
| 417: | 17193084 | g | a |
| 418: | 17194501 | c | t |
| 419: | 17209631 | a | t |
| 420: | 17219055 | a | c |
| 421: | 17220289 | g | a |
| 422: | 17238397 | a | g |
| 423: | 17244984 | t | c |
| 424: | 17248128 | g | a |
| 425: | 17257839 | c | t |
| 426: | 17262723 | c | g |
| 427: | 17278114 | t | c |
| 428: | 17281188 | c | t |
| 429: | 17290111 | g | a |
| 430: | 17316238 | t | c |
| 431: | 17333820 | t | c |
| 432: | 17335050 | t | a |
| 433: | 17343694 | g | a |
| 434: | 17367747 | t | c |
| 435: | 17369809 | c | t |
| 436: | 17370858 | g | a |
| 437: | 17373013 | t | c |
| 438: | 17373879 | a | g |

TABLE 3-continued

| POSITION | REFERENCE_BASE | ALTERNATE_BASE |
|---|---|---|
| 439: 17375880 | g | c |
| 440: 17379865 | t | c |
| 441: 17384067 | t | g |
| 442: 17393351 | t | a |
| 443: 17394036 | a | g |
| 444: 17396356 | g | a |
| 445: 17397743 | g | a |
| 446: 17398741 | a | g |
| 447: 17402470 | c | t |
| 448: 17412963 | a | g |
| 449: 17437115 | a | g |
| 450: 17473474 | c | t |
| 451: 17475236 | t | c |
| 452: 17480553 | c | t |
| 453: 17486157 | t | c |
| 454: 17501700 | t | g |
| 455: 17528110 | t | c |
| 456: 17547768 | g | a |
| 457: 17550231 | a | g |
| 458: 17553702 | g | c |
| 459: 17570023 | c | t |
| 460: 17571585 | t | a |
| 461: 17580847 | g | c |
| 462: 17614190 | c | t |
| 463: 17622058 | t | c |
| 464: 17625750 | c | t |
| 465: 17634579 | a | g |
| 466: 17639494 | c | g |
| 467: 17644090 | c | t |
| 468: 17647361 | c | t |
| 469: 17650880 | t | g |
| 470: 17651536 | a | g |
| 471: 17660174 | g | t |
| 472: 17660498 | c | g |
| 473: 17663768 | g | a |
| 474: 17667391 | c | t |
| 475: 17668368 | t | c |
| 476: 17668835 | t | c |
| 477: 17693107 | a | g |
| 478: 17694468 | a | t |
| 479: 17760514 | g | t |
| 480: 17761607 | g | c |
| 481: 17771810 | g | a |
| 482: 17773264 | a | g |
| 483: 17794236 | t | c |

TABLE 3-continued

| POSITION | REFERENCE_BASE | ALTERNATE_BASE |
|---|---|---|
| 484: 17794806 | t | a |
| 485: 17801640 | g | a |
| 486: 17810038 | c | t |
| 487: 17823360 | a | c |
| 488: 17875449 | t | c |
| 489: 17900831 | c | t |
| 490: 17902205 | t | a |
| 491: 17903237 | c | t |
| 492: 17910169 | c | t |
| 493: 17970301 | t | c |
| 494: 18001282 | t | g |
| 495: 18009431 | a | g |
| 496: 18009678 | a | t |
| 497: 18011006 | t | c |
| 498: 18011472 | c | t |
| 499: 18012518 | a | g |
| 500: 18016807 | a | g |
| 501: 18017043 | a | c |
| 502: 18018684 | t | c |
| 503: 18020417 | t | a |
| 504: 18021881 | a | t |
| 505: 18024253 | c | a |
| 506: 18025474 | g | a |
| 507: 18030960 | c | t |
| 508: 18031267 | c | t |
| 509: 18067382 | g | a |
| 510: 18072464 | c | t |
| 511: 18073416 | a | g |
| 512: 18078999 | c | t |
| 513: 18098017 | g | t |
| 514: 18101558 | a | g |
| 515: 18102008 | a | c |
| 516: 18158420 | g | a |

It is to be understood that the above description is illustrative and not restrictive. The scope of the invention should, therefore, be determined not with respect to the above description, but instead with respect to the appended claims, along with the full scope of equivalents to which the claims are entitled.

---

What is claimed is:

1. A method of performing genetic analysis comprising the steps of:
   a) scanning genomic DNA or derivatives therefrom from a plurality of individuals, wherein at least 10,000 bases are scanned, for genetic variants;
   b) identifying said genetic variants in said genomic DNA or derivatives therefrom that occur in a plurality of individuals;
   c) for at least said genomic variants that occur in a plurality of individuals, but not all of said at least 10,000 bases, scanning genomic DNA or derivatives therefrom from additional individuals to identify which of said genetic variants occur in said additional individuals; and
   d) based on the results of step c), identifying blocks of said variants.

2. A method as recited in claim 1 further comprising the step of using said blocks of variants in an association study, whereby said blocks of variants are associated with a phenotypic trait.

3. The method as recited in claim 2 further comprising the step of diagnosing said phenotypic trait using one or more variants that are in said block.

4. The method as recited in claim 2 further comprising the step of using said variants associated with a phenotypic trait to identify a potential drug target.

5. The method as recited in claim 4 further comprising the step of using said potential drug target in a small molecule screening process.

6. The method as recited in claim 1 wherein said step of scanning genomic DNA or derivatives therefrom comprises the steps of:
   a) forming an array of probes, wherein said array includes a) probes that are complementary to portions of a first sequence of said genomic DNA or derivative therefrom and b) probes that are complementary to variants of said genomic DNA or derivative therefrom;
   b) hybridizing said genomic DNA or derivative therefrom to said array; and
   c) identifying where said genomic DNA or derivative therefrom hybridize to said array.

7. A method as recited in claim 1 wherein said step of scanning genomic DNA comprises the step of sequencing said genomic DNA with a gel based sequencer.

8. The method as recited in claim 1 wherein said step of scanning genomic DNA comprises the step of sequencing said genomic DNA with a capillary based sequencer.

9. The method as recited in claim 1 wherein only variants that occur in more than 10% of the said plurality of individuals are used in step c).

10. The method as recited in claim 1 where said step of scanning genomic DNA to identify which of said variants occur in additional individuals comprises the steps of:
    a) exposing labeled genomic DNA or a derivative thereof corresponding to said additional individuals to a high density array of probes complementary to said variants; and
    b) determining where said genomic DNA hybridizes to said high density array, thereby identifying probes that are complementary to said variants that occur in said additional individuals and further, identifying which of said variants occur in said additional individuals.

11. The method as recited in claim 1 where said step of scanning genomic DNA to identify which is said variants occur in additional individuals comprises the use of an Invader assay.

12. The method as recited in claim 1 where said step of scanning genomic DNA to identify which is said variants occur in additional individuals comprises the use of a Taqman assay.

13. The method as recited in claim 1 wherein more than $1 \times 10^6$ bases are scanned for variants.

14. The method as recited in claim 1 wherein more than $1 \times 10^7$ bases are scanned for variants.

15. The method as recited in claim 1 wherein more than $1 \times 10^8$ bases are scanned for variants.

16. The method as recited in claim 1 wherein more than $1 \times 10^9$ bases are scanned for variants.

17. The method as recited in claim 1 wherein introns are scanned for variants.

18. The method as recited in claim 1 wherein introns and exons are scanned for variants.

19. The method as recited in claim 1 wherein more than 10% of all the non-repeat genomic DNA from the organism is scanned for variants.

20. The method as recited in claim 1 wherein more than 25% of all the non-repeat genomic DNA from an organism is scanned for variants.

21. The method as recited in claim 1 wherein more than 50% of all the non-repeat genomic DNA from an organism is scanned for variants.

22. The method as recited in claim 1 wherein more than 75% of all the non-repeat genomic DNA from an organism is scanned for variants.

23. The method as recited in claim 1 wherein said variants are single nucleotide polymorphisms.

24. The method as recited in claim 2 further comprising the step of using the results of the association study to stratify a patent population in a clinical trial.

25. The method as recited in claim 2 further comprising the step of using the results of the association study to stratify patents that respond to a drug from those who do not respond to a drug.

26. The method as recited in claim 2 further comprising the step of using the results of the association study to stratify patents that will show toxic response to a drug from patents that will not show toxic response to a drug.

* * * * *

SEQUENCE LISTING

<160> NUMBER OF SEQ ID NOS: 8

<210> SEQ ID NO 1
<211> LENGTH: 13
<212> TYPE: DNA
<213> ORGANISM: Artificial
<220> FEATURE:
<223> OTHER INFORMATION: HYPOTHETICAL SEQUENCE

<400> SEQUENCE: 1
agattcgata acg                                                          13

<210> SEQ ID NO 2
<211> LENGTH: 13
<212> TYPE: DNA
<213> ORGANISM: artificial
<220> FEATURE:
<223> OTHER INFORMATION: HYPOTHETICAL SEQUENCE

<400> SEQUENCE: 2
agactacata acg                                                13

<210> SEQ ID NO 3
<211> LENGTH: 13
<212> TYPE: DNA
<213> ORGANISM: artificial
<220> FEATURE:
<223> OTHER INFORMATION: HYPOTHETICAL SEQUENCE

<400> SEQUENCE: 3
tatttcgata acg                                                13

<210> SEQ ID NO 4
<211> LENGTH: 13
<212> TYPE: DNA
<213> ORGANISM: artificial
<220> FEATURE:
<223> OTHER INFORMATION: HYPOTHETICAL SEQUENCE

<400> SEQUENCE: 4
tatctacaat cac                                                13

<210> SEQ ID NO 5
<211> LENGTH: 13
<212> TYPE: DNA
<213> ORGANISM: artificial
<220> FEATURE:
<223> OTHER INFORMATION: HYPOTHETICAL SEQUENCE

<400> SEQUENCE: 5
actgacccct ttt                                                13

<210> SEQ ID NO 6
<211> LENGTH: 13
<212> TYPE: DNA
<213> ORGANISM: artificial
<220> FEATURE:
<223> OTHER INFORMATION: HYPOTHETICAL SEQUENCE

<400> SEQUENCE: 6
agtaacccct ttt                                                13

<210> SEQ ID NO 7
<211> LENGTH: 13
<212> TYPE: DNA
<213> ORGANISM: ARTIFICIAL
<220> FEATURE:
<223> OTHER INFORMATION: HYPOTHETICAL SEQUENCE

<400> SEQUENCE: 7
actgacccct ttt                                                13

<210> SEQ ID NO 8
<211> LENGTH: 13
<212> TYPE: DNA
<213> ORGANISM: ARTIFICIAL
<220> FEATURE:
<223> OTHER INFORMATION: HYPOTHETICAL SEQUENCE

<400> SEQUENCE: 8
actgactctt taa                                                13